United States Patent
Brown

(10) Patent No.: US 11,254,649 B2
(45) Date of Patent: *Feb. 22, 2022

(54) CRYSTALLINE FUMARATE SALT OF (S)-[3,4-DIFLUORO-2-(2-FLUORO-4-IODOPHENYLAMINO)PHENYL] [3-HYDROXY-3-(PIPERIDIN-2-YL) AZETIDIN-1-YL]-METHANONE

(71) Applicant: Exelixis, Inc., Alameda, CA (US)

(72) Inventor: Adrian St. Clair Brown, Ely (GB)

(73) Assignee: Exelixis, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,161

(22) Filed: Jan. 17, 2020

(65) Prior Publication Data

US 2020/0255398 A1    Aug. 13, 2020

Related U.S. Application Data

(63) Continuation of application No. 15/852,280, filed on Dec. 22, 2017, now Pat. No. 10,590,102, which is a continuation of application No. PCT/US2016/040444, filed on Jun. 30, 2016.

(60) Provisional application No. 62/187,009, filed on Aug. 30, 2015.

(51) Int. Cl.
*C07D 401/04*    (2006.01)
*A61P 35/02*    (2006.01)

(52) U.S. Cl.
CPC ............ *C07D 401/04* (2013.01); *A61P 35/02* (2018.01); *C07B 2200/13* (2013.01)

(58) Field of Classification Search
CPC .................. C07D 401/04; C07B 2200/13
See application file for complete search history.

(56) References Cited

U.S. PATENT DOCUMENTS

| | | |
|---|---|---|
| 7,803,839 B2 | 9/2010 | Aay et al. |
| 7,915,250 B2 | 3/2011 | Aay et al. |
| 7,956,191 B2 | 6/2011 | Abel et al. |
| 7,999,006 B2 | 8/2011 | Lamb et al. |
| 8,362,002 B2 | 1/2013 | Aay et al. |
| 8,642,584 B2 | 2/2014 | Aftab et al. |
| 9,771,347 B2 | 9/2017 | Naganathan et al. |
| 10,239,858 B2 | 3/2019 | Naganathan et al. |
| 10,590,102 B2 | 3/2020 | Brown |
| 2010/0075947 A1 | 3/2010 | Aftab et al. |
| 2014/0100215 A1 | 4/2014 | Aftab et al. |
| 2014/0271634 A1 | 9/2014 | Sliwkowski et al. |
| 2014/0275527 A1 | 9/2014 | Aay et al. |
| 2015/0141399 A1 | 5/2015 | Aay et al. |
| 2019/0185447 A1 | 6/2019 | Naganathan et al. |

FOREIGN PATENT DOCUMENTS

| | | |
|---|---|---|
| WO | 2006127926 A2 | 11/2006 |
| WO | 2007044515 A1 | 4/2007 |
| WO | 2008076415 A1 | 6/2008 |
| WO | 2008124085 A2 | 10/2008 |
| WO | 2014138279 A1 | 9/2014 |

OTHER PUBLICATIONS

Yu, et al., "Physical Characterization of Polymorphic Drugs: An Integrated Characterization Strategy", Pharmaceutical Science and Technology Today, Elsevier Trends Journals, Cambridge, GB, vol. 1, No. 3, Jun. 1, 1998 (Jun. 1, 1998), pp. 118-127.
Berge et al., "Pharmaceutical salts," J Pharm. Sci., 66 (1): 1-19 (Jan. 1977).
Morissette, S. High-throughput crystallization: polymorphs, salts, co-crystals and solvates of pharmaceutical solids. Advanced Drug Deliver Reviews, 56(3), 275-300. doi:10.1016/j.addr.2003.10.020.
Caira, M. "Crystalline Polymorphism of Organic Compounds", Topics in Current Chemistry, vol. 198, Springer Verlag Berlin Heidelberg, 1998.
Methods Validation Report Summary (Cobimetinib, 20 mg tablet, NDA 206192, May 20, 2015).
International Search Report of PCT/US2016/040444, dated Aug. 12, 2016.
Ashizawa, Kazuhide. The Science of Polymorphism and Crystallization of Medicaments.
Brittain, H.G. "Polymorphism in pharmaceutical solids", 2009.
Hirayama, Noriaki. Organic Compound Crystal Formulation Handbook.
Larkin, J, et al. "Combined Vemurafenib and Cobimetinib in BRAF-Mutated Melanoma", The New England Journal of Medicine, vol. 371, No. 20, Nov. 13, 2014. pgs. 1867-1876.
Philip L.Gould: "Salt selection for basic drugs", Pharmaceutical Research and Development Department, Pfizer Central Research, Sandwich, Kent (U.K), International Journal of Pharmaceutics, 33(1986), pp. 201-217.
Richard J.Bastin, Michael J. Bowker and Bryan J. Slater : "Salt Selection and Optimisation Procedures for Pharmaceutical New Chemical Entities", Organic Process Research & Development, 2000, 4, pp. 427-435.
Serajuddin, Abu T. M. "Salt formation to improve drug solubility", Advanced Drug Reviews, 2007, vol. 59, p. 603-616.

(Continued)

*Primary Examiner* — Kamal A Saeed
(74) *Attorney, Agent, or Firm* — Honigman LLP; Heidi M. Berven; Andrew S. Chipouras

(57) ABSTRACT

This disclosure relates to the crystalline fumarate salt of (S)[3,4-difluoro-2-(2-fluoro-4-iodophenylamino)phenyl] [3-hydroxy-3-(piperidin-2-yl) azetidin-1-yl]-methanone. The disclosure also relates to pharmaceutical compositions comprising the crystalline fumarate salt of (S)[3,4-difluoro-2-(2-fluoro-4-iodophenylamino)phenyl] [3-hydroxy-3-(piperidin-2-yl) azetidin-1-yl]-methanone. The disclosure also relates to methods of treating cancers comprising administering to a patient in need thereof the crystalline fumarate salt of (S)-[3,4-difluoro-2-(2-fluoro-4-iodophenylamino) phenyl] [3-hydroxy-3-(piperidin-2-yl) azetidin-1-yl]-methanone.

15 Claims, 13 Drawing Sheets

(56) References Cited

OTHER PUBLICATIONS

Vladimirova L. Yu, Usage of Mek Inhbitors in Oncology: Results and Perspectives, Advances in Current Natural Sciences, 2015, vol. 3, pp. 18-30.
Wermuth, C.G. (ed). The Practice of Medicinal Chemistry, Technomics.
Paulekuhn et al., J Med Chem 50(26), 6665-6672 (2007).
Correa, Carlos. "Guidelines for the examination of pharmaceutical patents, a public health perspective", WHO-ICTSD-UNCTAD, Mar. 2008, pp. 9-11.
Kawaguchi, Yoko et al. "Drug and Crystal Polymorphism." Journal of Human Environmental Engineering, vol. 4, No. 2, 2002, pp. 310-317.
Moribe, Kunikazu, et al. Cryobiology and Cryotechnology, vol. 51, No. 1, 2005, pp. 19-24.

CRYSTALLINE FUMARATE SALT OF (S)-[3,4-DIFLUORO-2-(2-FLUORO-4-IODOPHENYLAMINO)PHENYL] [3-HYDROXY-3-(PIPERIDIN-2-YL) AZETIDIN-1-YL]-METHANONE

CROSS-REFERENCE TO RELATED APPLICATIONS

This application is a continuation application of U.S. Ser. No. 15/852,280, filed Dec. 22, 2017, which is a continuation of international application number PCT/US2016/040444, filed Jun. 30, 2016, which claims the benefit of U.S. provisional patent application Ser. No. 62/187,009, filed Jun. 30, 2015, all of which are incorporated herein by reference in their entirety.

TECHNICAL FIELD

This disclosure relates to the crystalline fumarate salt of (S)-[3,4-difluoro-2-(2-fluoro-4-iodophenylamino)phenyl] [3-hydroxy-3-(piperidin-2-yl) azetidin-1-yl]-methanone. The disclosure also relates to pharmaceutical compositions comprising the crystalline fumarate salt of (S)-[3,4-difluoro-2-(2-fluoro-4-iodophenylamino)phenyl] [3-hydroxy-3-(piperidin-2-yl) azetidin-1-yl]-methanone. The disclosure also relates to methods of treating cancers comprising administering to a patient in need thereof the crystalline fumarate salt of (S)-[3,4-difluoro-2-(2-fluoro-4-iodophenylamino) phenyl] [3-hydroxy-3-(piperidin-2-yl) azetidin-1-yl]-methanone.

BACKGROUND

Traditionally, dramatic improvements in the treatment of cancer are associated with identification of therapeutic agents acting through novel mechanisms. One mechanism that can be exploited in cancer treatment is the modulation of MEK (MAPK/ERK Kinase). MEK inhibition represents a promising strategy for treating cancers caused by aberrant ERK/MAPK pathway signaling (Solit et al., 2006; Wellbrock et al., 2004). The MEK-ERK signal transduction cascade is a conserved pathway which regulates cell growth, proliferation, differentiation, and apoptosis in response to growth factors, cytokines, and hormones. This pathway operates downstream of Ras which is often upregulated or mutated in human tumors. MEK is a critical effector of Ras function. The ERK/MAPK pathway is upregulated in 30% of all tumors, and oncogenic activating mutations in K-Ras and B-Raf have been identified in 22% and 18% of all cancers respectively (Allen et al., 2003; Bamford S, 2004; Davies et al., 2002; Malumbres and Barbacid, 2003). A large portion of human cancers, including 66% (B-Raf) of malignant melanomas, 60% (K-Ras) and 4% (B-Raf) of pancreatic cancers, 50% of colorectal cancers (colon, in particular, K-Ras: 30%, B-Raf: 15%), 20% (K-Ras) of lung cancers, 27% (B-Raf) of papillary and anaplastic thyroid cancer, and 10-20% (B-Raf) of endometrioid ovarian cancers, harbor activating Ras and Raf mutations. Inhibition of the ERK pathway, and in particular inhibition of MEK kinase activity, results in anti-metastatic and anti-angiogenic effects largely due to a reduction of cell-cell contact and motility as well as downregulation of vascular endothelial growth factor (VEGF) expression. Furthermore, expression of dominant negative MEK or ERK reduced the transforming ability of mutant Ras as seen in cell culture and in primary and metastatic growth of human tumor xenografts in vivo. Therefore, the MEK-ERK signal transduction pathway is an appropriate pathway to target for therapeutic intervention and compounds that target MEK present considerable therapeutic potential.

One compound that specifically inhibits MEK is (S)-[3,4-difluoro-2-(2-fluoro-4-iodophenylamino)phenyl] [3-hydroxy-3-(piperidin-2-yl) azetidin-1-yl]-methanone (Compound I), which has the chemical structure:

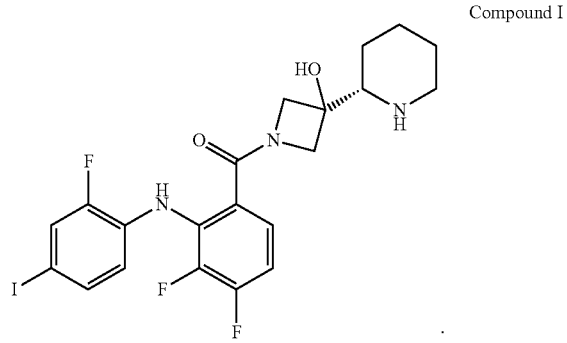 [SMILES: O=C(c1ccc(F)c(F)c1Nc1ccc(I)cc1F)N1CC(O)([C@@H]2CCCCN2)C1]

Compound I

WO 2007/044515 describes the synthesis of (S)-[3,4-difluoro-2-(2-fluoro-4-iodophenylamino)phenyl] [3-hydroxy-3-(piperidin-2-yl) azetidin-1-yl]methanone (Example 22b, page 231) and also discloses the therapeutic activity of this molecule to inhibit, regulate and/or modulate MEK (Biochemical Assay, page 268). Compound I has been approved in the United States, Europe, and elsewhere for the treatment of melanoma in combination with vemurafenib (Zelboraf®).

Besides therapeutic efficacy, a drug developer endeavors to provide a suitable form of the therapeutic agent that has properties appropriate for processing, manufacturing, storage stability, and/or usefulness as a drug. Accordingly, the discovery of a form that possesses some or all of these desired properties is important to drug development.

Applicants have discovered a crystalline salt form of the Compound I that has suitable properties for use in a pharmaceutical composition for the treatment of proliferative diseases such as cancer.

SUMMARY

This disclosure relates to the crystalline fumarate salt of Compound I as described herein. The fumarate salt of Compound I has the following structure and has been identified as a hemifumarate:

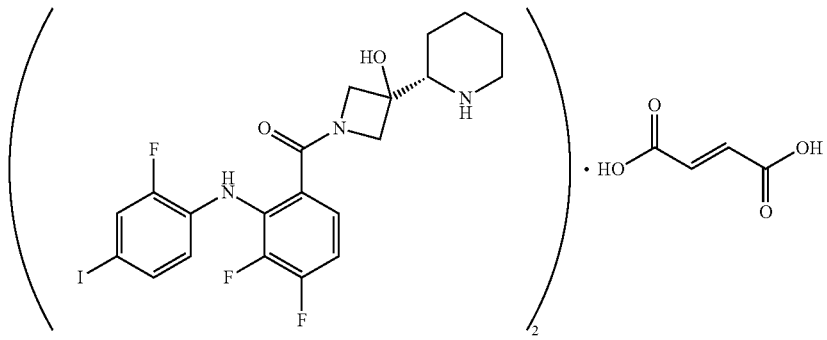

This disclosure also relates to pharmaceutical compositions comprising a crystalline fumarate salt of Compound I.

This disclosure also relates uses of the crystalline fumarate salt of Compound I.

DETAILED DESCRIPTION

This disclosure relates to a crystalline fumarate salt of Compound I. The invention also relates to novel compositions comprising the disclosed crystalline fumarate salt of Compound I. Therapeutic uses of the crystalline fumarate salt of Compound I as described as well as therapeutic compositions containing them represent separate aspects of the disclosure. The techniques used to characterize the crystalline fumarate salt of Compound I are described in the examples below. These techniques, alone or in combination, may be used to characterize the crystalline fumarate salt of Compound I. The crystalline fumarate salt of Compound I may be also characterized by reference to the disclosed figures.

The crystalline fumarate salt of Compound I was found to be thermodynamically stable, was the only crystalline form identified after extensive experimentation, is non-hygroscopic and is consistently formed in manufacturing. In contrast, the amorphous form is non-crystalline, hygroscopic and converts to crystalline Form A. In addition, when trying to make salts of Compound I, only the fumarate provided a single crystalline form. Other salts that could be made were amorpohous or a mixture of crystalline and amorphous materials.

Crystalline Fumarate Salt of Compound I

This disclosure relates to the crystalline fumarate salt of Compound I. This disclosure also relates to pharmaceutical compositions of the crystalline fumarate salt of Compound I. The fumarate salt can be made by combining (S)-[3,4-difluoro-2-(2-fluoro-4-iodophenylamino)phenyl] [3-hydroxy-3-(piperidin-2-yl) azetidin-1-yl-methanone (Compound I) with fumaric acid, which forms a salt having 2:1 Compound I:fumaric acid stoichiometry. The crystalline fumarate salt of Compound I can also be referred to as a hemifumarate.

Fumaric acid has the following structure:

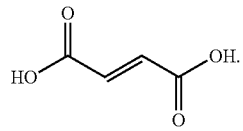

There are various names for Compound I, including, XL518, GDC-0973, [3,4-difluoro-2-(2-fluoro-4-iodoanilino)phenyl]{3-hydroxy-3-[(2S)-piperidin-2-yl]azetidin-1-yl} methanone, cobimetinib, and Cotellic™.

Compound I can be prepared according to any of several different methodologies, either on a gram scale (<1 kg) or a kilogram scale (>1 kg). A gram-scale method is set forth in WO 2007/044515, which describes the synthesis of Compound I (Examples 22b), which document is hereby incorporated by reference in its entirety. Alternatively, Compound I can be prepared on a kilogram scale using the procedure set forth in WO 2014/059422, which is also incorporated by reference herein in its entirety, and as provided in the Examples below.

Form A has a water solubility of 1.6 mg/mL at 25° C. Under the conditions of 25° C/0% relative humidity (RH) and 25° C/90% RH, Form A showed no change in assay, purity, moisture and dissolution. The DSC showed Form A to be stable up to the melting point of 239° C. No solvent losses were observed.

Figure 2:
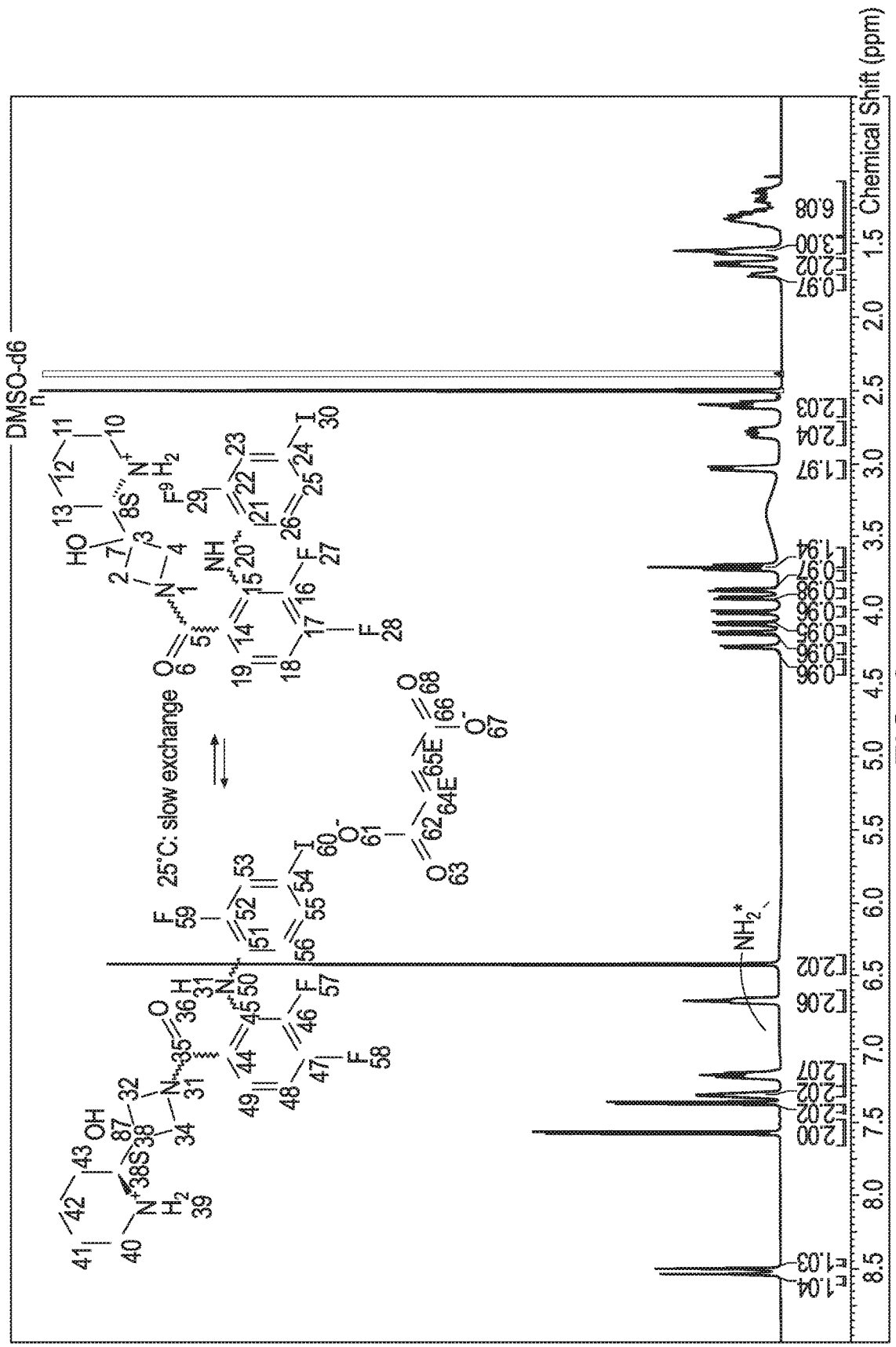
FIG. 2 shows the $^1$H NMR spectrum in DMSO-$d_6$ of the crystalline fumarate salt of Compound I, designated as Form A.
Figure 3:
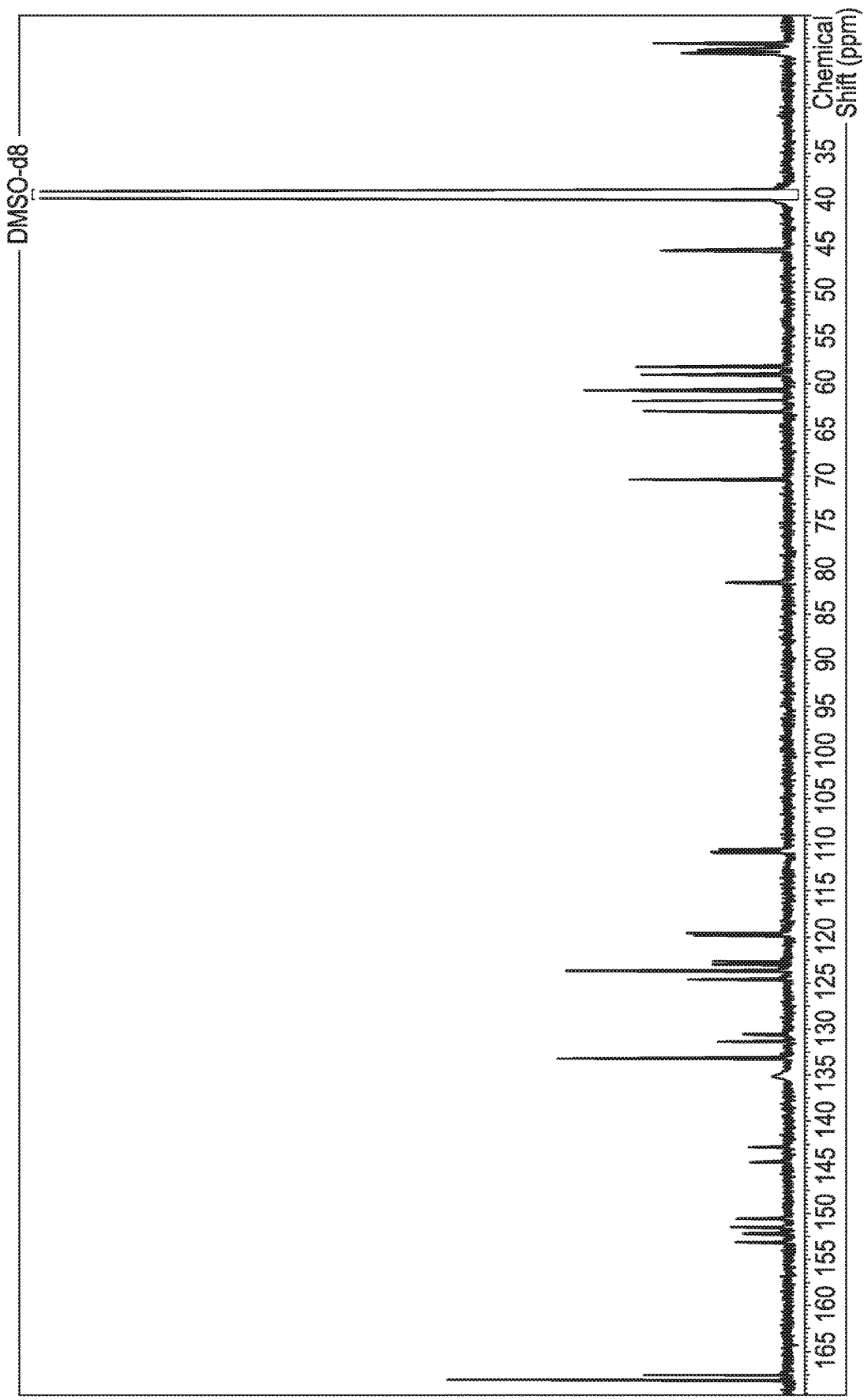
FIG. 3 shows the $^{13}$C NMR spectrum in DMSO-$d_6$ of the crystalline fumarate salt of Compound I, designated as Form A.
Figure 4:
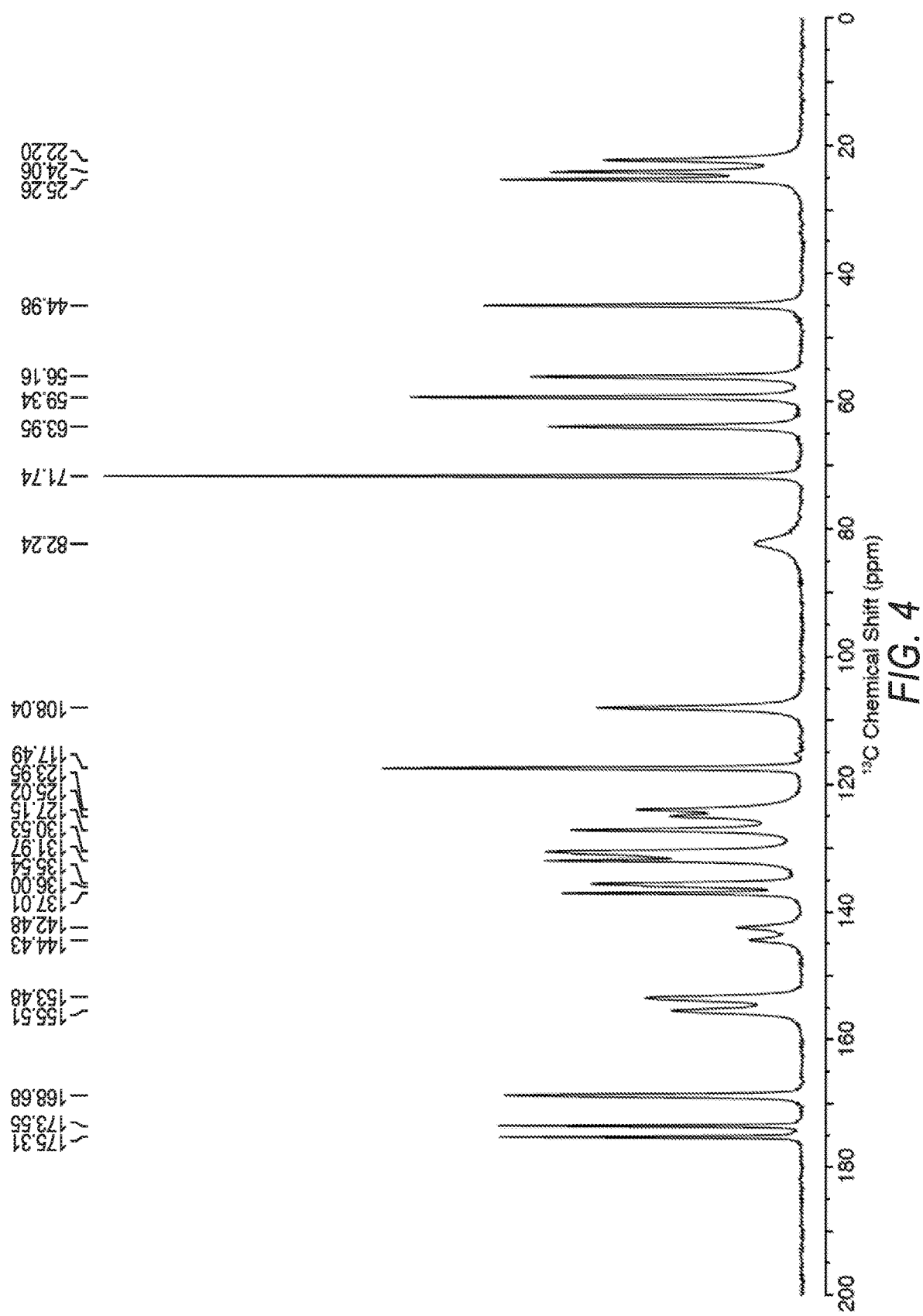
FIG. 4 shows the $^{13}$C NMR solid state spectrum of the crystalline fumarate salt of Compound I, designated as Form A.

Form A as described herein may be characterized by at least one of the following:
(i) a $^1$H NMR spectrum in $d_6$ DMSO substantially as depicted in FIG. 2;
(ii) a 13C NMR spectrum in $d_6$ DMSO substantially as depicted in FIG. 3;
(iii) a solid state $^{13}$C NMR spectrum with three or more peaks selected from 175.3, 173.6, 117.5, 155.5, and 153.5, ± 0.2 ppm;
(iv) a solid state $^{13}$C NMR spectrum substantially as depicted in FIG. 4;
(v) a powder x-ray diffraction pattern (CuKα λ=1.5418 Å) comprising three or more 2θ values selected from 4.6, 12.1, 13.2, 13.6 and 14.5 ± 0.2 °2θ, wherein measurement of the crystalline form is at room temperature;
(vi) an x-ray powder diffraction (XRPD) pattern substantially in accordance with the pattern shown in FIG. 10; and
(vii) a differential scanning calorimetry thermogram substantially in accordance with FIG. 8.

In one embodiment, Form A is characterized by at least two of (i), (ii), (iii), (iv), (v), (vi), or (vii).

In another embodiment, Form A is characterized by at least three of (i), (ii), (iii), (iv), (v), (vi), or (vii).

In another embodiment, Form A is characterized by at least four of (i), (ii), (iii), (iv), (v), (vi), or (vii).

In another embodiment, Form A is characterized by at least five of (i), (ii), (iii), (iv), (v), (vi), or (vii).

In another embodiment, Form A is characterized by at least six of (i), (ii), (iii), (iv), (v), (vi), or (vii).

In another embodiment, Form A is characterized by all of (i), (ii), (iii), (iv), (v), (vi), or (vii).

In one embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two three, four, or five peaks selected from 175.3, 173.6, 117.5, 155.5, and 153.5, ± 0.2 ppm in the solid state $^{13}$C NMR spectrum.

In another embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one or more peaks selected from 173.6, 117.5, 155.5, and 153.5, ± 0.2 ppm solid state $^{13}$C NMR spectrum.

In another embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three or four peaks selected from 175.3, 117.5, 155.5, and 153.5, ± 0.2 ppm solid state $^{13}$C NMR spectrum.

In another embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three or four peaks selected from 175.3, 173.6, 155.5, and 153.5, ± 0.2 ppm solid state $^{13}$C NMR spectrum.

In another embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three or four peaks selected from 175.3, 173.6, 117.5, and 153.5, ± 0.2 ppm solid state $^{13}$C NMR spectrum.

In one embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three or four peaks selected from 175.3, 173.6, 117.5, and 155.5, ± 0.2 ppm solid state $^{13}$C NMR spectrum.

In one embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three, four, or five peaks selected from 4.6, 12.1, 13.2, 13.6 and 14.5 ± 0.2 °2θ in the x-ray diffraction pattern (CuKα λ=1.5418 Å).

In another embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three, or four peaks selected from 12.1, 13.2, 13.6 and 14.5 ± 0.2 °2θ in the x-ray diffraction pattern (CuKα λ=1.5418 Å).

In another embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three, or four peaks selected from 4.6, 12.1, 13.6 and 14.5 ± 0.2 °2θ in the x-ray diffraction pattern (CuKα λ=1.5418 Å).

In another embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three, or four peaks selected from 4.6, 13.6 and 14.5 ± 0.2 °2θ in the x-ray diffraction pattern (CuKα λ=1.5418 Å).

In one embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two, three, or four peaks selected from 4.6, 12.1, 13.2, and 13.6 ± 0.2 °2θ in the x-ray diffraction pattern (CuKα λ=1.5418 Å).

Other solid state properties which may be used to characterize the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A are shown in the figures and discussed in the examples below.

In one embodiment, the crystalline fumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by unit cell parameters approximately equal to the following:

Crystal System: Tetragonal
Space Group: P43212
Crystal Habit: Plates
Unit Cell Dimensions
a=7.8825 Å
b=7.8825 Å
c=76.846 Å
α=90°
β=90°

γ=90°
Temperature: 293 K
Cell Volume: 4774.7 Å$^3$
Molecules in Unit Cell: 8
Density: 1.637 g/cm$^3$ The unit cell parameters of Form A were measured at a temperature of approximately 25° C., e.g., ambient or room temperature.

In another embodiment, the disclosure relates to Form A as described herein in any of the aspects and/or embodiments, in substantially pure form.

The disclosure also relates to a process for preparing the crystalline fumarate salt of Compound I designated as Form A. The preparation, solid state properties, and characteristics of the crystalline fumarate salt of Compound I designated as Form A are described in the examples below.

Pharmaceutical Compositions

Another aspect of this disclosure relates to a pharmaceutical composition comprising the crystalline fumarate salt of Compound I, and one or more pharmaceutically acceptable excipients. The amount of the crystalline fumarate salt of Compound I can be a therapeutically effective amount. Another aspect of this disclosure relates to a solid or dispersion pharmaceutical composition comprising the crystalline fumarate salt of Compound I, or combinations thereof, and a pharmaceutically acceptable excipient.

In one embodiment, the formulation is a tablet formulation. Tablets are generally formed from the drug active, filler, disintegrant and lubricant by blending, granulation and tableting.

Fillers are known in the art and include, for instance and without limitation, sugars and sugar alcohols, cellulosics, and other fillers. Non-limiting examples of suitable sugars and sugar alcohols include dextrates, dextrin, dextrose, lactose, maltodextrin, mannitol, isomalt, sorbitol, sucrose, sugars spheres, xylitol, fructose, lactitol, erythritol, maltitol, xylose, glucose, mannose, galactose, maltose, cellobiose, trehalose and raffinose. Non-limiting examples of cellulosics include microcrystalline cellulose ("MCC") and silicified MCC. Non-limiting examples of other fillers include calcium carbonate, calcium sulphate, calcium silicate, chitin, chitosan, dibasic calcium phosphate dihydrate, glyceryl palmitostearate, hydrogenated vegetable oil, kaolin, magnesium aluminum silicate, magnesium carbonate, magnesium oxide, polymethacrylates, potassium chloride, powdered cellulose, pregelatinized starch, sodium chloride, starch, talc, and di- and tri-basic calcium phosphate. In some aspects of the disclosure, the filler is lactose, MCC, silicified MCC, di-basic calcium phosphate, mannitol, isomalt, pregelatinized starch, and combinations thereof.

Disintegrants are known in the art. Non-limiting examples include: modified starches such as sodium carboxymethyl starch (sodium starch glycolate); cross-linked polyvinylpyrrolidones such as crospovidone; modified celluloses such as croscarmellose sodium; cross-linked alginic acid; gums such as gellan gum and xanthan gum; calcium silicate. In some aspects of the disclosure, the disintegrant is croscarmellose sodium, crospovidone, sodium starch glycolate, and combinations thereof. In some aspects of the disclosure, the disintegrant is croscarmellose sodium, sodium starch glycolate, and combinations thereof.

Lubricants are known in the art. Non-limiting examples include magnesium stearate, calcium stearate, stearic acid, sodium stearyl fumarate, hydrogenated vegetable oils, polyethylene glycol (4000-6000), and sodium lauryl sulfate. In some aspects of the disclosure, the lubricant is magnesium stearate, sodium stearyl fumarate, and combinations thereof.

In one tablet manufacturing aspect of the present disclosure, filler, disintegrant and lubricant are delumped by passing through screen to form delumped pre-blend material. Delumped pre-blend material is combined with an active drug in a blending apparatus and admixed to form a pre-blend. The pre-blend is granulated in a dry granulation apparatus (e.g., by granulation, milling and screening) to form granules. The filler, disintegrant and lubricant are present in granules as intragranular components. Additional disintegrant and lubricant are delumped by passing through a screen to form delumped material that is combined with the granules in a blending apparatus, and admixed to form a final blend. The final blend is tableted in a tableting apparatus to form core tablets. The core tablets are coated with a coating mixture in a film coating apparatus to form coated tablets.

As used herein, intragranular refers to a component that is added prior to granulation such that the component is incorporated within the granules. As further used herein, extragranular refers to a component that is combined with the granules prior to compression, such as in a tablet press.

In another tablet manufacturing process of the present disclosure, intragranular filler and intragranular disintegrant are delumped by screening and combined with an active drug in a blender apparatus. The components are then admixed to form a primary pre-blend. Intragranular lubricant is delumped by screening and is combined with the primary pre-blend in a blender apparatus. The components are then admixed to form the pre-blend. The pre-blend is dry granulated in a granulator apparatus by granulation, milling and screening to form granules. Extragranular disintegrant is delumped by screening and is combined with the granules in a blender apparatus. The components are then admixed to form a primary final blend. Extragranular lubricant is delumped by screening and is combined with the primary final blend in a blender apparatus. The components are then admixed to form a final blend. The final blend is tableted in a tableting apparatus to form core tablets. A film-coat solid mixture is combined with water and suspended in a suspending apparatus to form film-coating mixture. The core tablets are coated with the coating mixture in a film coating apparatus to form coated tablets.

One particular manufacturing aspect of the present disclosure comprises the following pre-blending, granulating/milling and screening, final blending, tableting, and coating steps. A pre-blend is formed in two steps. In a first step, intragranular lactose monohydrate, intragranular croscarmellose sodium, and intragranular microcrystalline cellulose are screened for delumping and charged to a blender. Delumping may be done by methods known to those skilled in the art such as passing the material through a 1.0 mm mesh screen as using a vibratory sifter or an in-line sifter. Cobimetinib hemifumarate Form A is then charged to the blender, and the blender contents are admixed at a blending speed of 6 rpm for 30 minutes. In a second step, intragranular magnesium stearate is screened for delumping through a 0.5 mm mesh screen and charged to the blender, and the contents are admixed at a blending speed of 6 rpm for 8 minutes to produce the pre-blend. In some such aspects, a pre-blend batch suitable for producing 420,000 tablets is manufactured wherein the pre-blend comprises 22.982 kg microcrystalline cellulose, 15.322 kg lactose monohydrate, 1.008 kg croscarmellose sodium and 0.126 kg magnesium stearate. The pre-blend is dry-granulated by roller compaction, milled and screened through a 1 mm screen. In some such aspects, for an active drug having a particle size D [v, 0.5] less than 38 μm, the roller compaction force is set at 2 kN/cm and the gap size is 5 mm. In some other such aspects, for an active drug having a particle size D [v, 0.5] of at least 38 μm, the roller compaction is set at from 2 kN/cm to 4 kN/cm and the gap size is from 4 mm to 5 mm. A final blend is formed in two steps. In a first step, extragranular croscarmellose sodium is screened through a 1.0 mm screen for delumping as described above and combined with the granulate in a blender. The blender contents are admixed at a blending speed of 6 rpm for 10 minutes. In a second step, extragranular magnesium stearate is screened through a 0.5 mm screen for delumping and charged to the blender, and the contents are admixed at 6 rpm for 8 minutes to form the final blend. In aspects wherein a final blend batch suitable for producing 420,000 tablets is manufactured, the amount of extragranular croscarmellose sodium is 1.008 kg and the amount of extragranular magnesium stearate 0.63 kg. The final blend is compressed in a press, such as a rotary tableting press, at a main compression force of from 14 kN to 19 kN to form tablet cores. The tablet cores are coated by spraying with a coating suspension using a pan coating apparatus known in the art. In some such aspects, wherein a final blend batch suitable for producing 420,000 tablets is manufactured, the coating suspension comprises 0.806 kg polyvinyl alcohol, 0.504 kg titanium dioxide, 0.407 kg Macrogol/PEG 3350, 0.298 kg talc and a suitable amount of purified water to form the coating suspension. In some other such aspects, the coating composition is Opadry II White 85F18422. Batch sizes other than those suitable for preparing 420,000 tablets may be prepared with the same ratios of ingredients.

Suitable blenders are known in the art and include any apparatus typically employed in the pharmaceutical industry for uniformly admixing two or more components including V-shaped blenders, double-cone blenders, bin (container) blenders, and rotary drum blenders. The combination blender volume, blender fill, rotation speed and rotation time may be suitably determined by those skilled in the art, based on routine experimentation, to achieve an essentially homogeneous admixture of components. Blender volume is suitably 50 L, 100 L, 200 L, 250 L or greater. Selection of blender fill allows for convection and three-dimensional material movement and is suitably about 25%, about 30%, about 35%, about 40%, about 50%, about 60% or about 70%, and ranges thereof, such as from about 30% to about 60%, from about 45% to about 65%, from 32% to 53% or from 32% to 40%. Blend time is suitably, 5 min, 10 min, 15 min, 20 min, 30 min, 40 min, 50 min, 60 min, or more. Rotation rate is suitably, for instance, 2 rpm, 3 rpm, 4 rpm, 5 rpm, 6 rpm, 7 rpm, 8 rpm, 9 rpm or 10 rpm.

Dry granulation, milling and screening equipment is known in the art and is available commercially from a number of manufacturers including Gertis, Fitzpatrick®, and Fruend-Vector. Such equipment generally provides for control of roller compaction force, gap width, roller speed and feed rate. The roller surfaces may be smooth, knurled, or one roller surface may be smooth and the other roller surface may be knurled. In any of the various aspects, the pre-blend is charged to a roller compactor feed hopper. Roller compaction is performed at a specified force and gap size, and the process is preferably run under gap control. The formed ribbons are milled through a screen to produce granules. In some aspects of the disclosure, the screen is integral to the mill. The gap size is suitably about 2 mm, about 3 mm, about 4 mm or about 5 mm, and ranges thereof, such as from about 2 mm to about 5 mm, from about 2 mm to about 4 mm, from about 3 mm to about 5 mm or from about 4 mm to about 5 mm. The roller compaction force is suitably about 1 kN/cm, about 2 kN/cm, about 3 kN/cm, about 4 kN/cm, about 5 kN/cm, about 6 kN/cm, about 7 kN/cm or about 8 kN/cm, and ranges thereof, such as from about 1 kN/cm to about 8 kN/cm, from about 2 kN/cm to about 5 kN/cm or from about 2 kN/cm to about 4 kN/cm. The milling screen size is suitably 0.5 mm, 0.75mm, 1.0 mm, 1.25 mm, 1.5 mm, 1.75mm, 2.0 mm, 2.25 mm or 2.5 mm, and ranges thereof, such as from about 0.5 mm to about 2.5 mm, from about 0.5 mm to about 2.0 mm, from about 0.5 mm to about 1.5 mm, from about 0.5 mm to about 1.25 mm, from about 0.75 mm to about 2.5 mm, from about 0.75 mm to about 2.0 mm, from about 0.75 mm to about 1.5 mm, from about 0.75 mm to about 1.25 mm. In some particular aspects of the disclosure, a 1.0 mm milling screen is used.

Suitable tablet presses are known in the art and are available commercially from, for instance, Riva-Piccola, Fette, Bosch Packaging Technology, GEA and Natoli Engineering Company. Generally, each tablet is made by pressing the granules inside a die, made up of hardened steel. The die is a disc shape with a hole cut through its center. The powder is compressed in the center of the die by two hardened steel punches that fit into the top and bottom of the die thereby forming the tablet. Tablet compression may be done in two stages with the first, pre-compression, stage involving tamping down the powder and compacting the blend slightly prior to application of the main compression force for tablet formation. The tablet is ejected from the die after compression. In some aspects of the disclosure, the compression force is about 5 kN, about 6 kN, about 7 kN, about 8 kN, about 9 kN, about 10 kN, about 11 kN, about 12 kN, about 13 kN, about 14 kN, about 15 kN, about 16 kN, about 17 kN, about 18 kN, about 19 kN or about 20 kN, and ranges thereof, such as from about 5 kN to about 20 kN, from about 14 kN to about 19 kN, from about 14 kN to about 18 kN, or from about 8 kN to about 13 kN. In some aspects of the disclosure, tablets comprising about 60 mg of the active drug may be formed at a compression force of from about 14 kN to about 18 kN. In other aspects of the disclosure, tablets comprising about 20 mg of the active drug may be formed at a compression force of from about 8 kN to about 13 kN.

In some aspects, the tablet core comprises the components and concentration ranges in wt. % as indicated in Table A.

TABLE A

| Component | $1^{st}$ Range | $2^{nd}$ Range | $3^{rd}$ Range |
|---|---|---|---|
| Active drug | 5-35% | 10-30% | 15-25% |
| Filler | 60-78% | 65-78% | 70-78% |
| Disintegrant | 1-7% | 2-6% | 3-5% |
| Lubricant | 0.5-5% | 1-4% | 1-3% |
| Binder (Optional) | 0-10% | 0-8% | 0-6% |

In some aspects of the present disclosure, the tablet core comprises the components and concentration ranges in wt. % as indicated in Table B on the basis of a tablet containing 20 mg of the active drug. For tablets comprising other than 20 mg of the active drug, e.g., 40 mg or 60 mg, the ratios of the various components disclosed below for the 20 mg tablets is maintained.

TABLE B

| Component | $1^{st}$ Range | $2^{nd}$ Range | $3^{rd}$ Range |
|---|---|---|---|
| Active drug | 17.5-18.5% | 17.5-18.5% | 17.5-18.5% |
| Filler | 60-78% | 65-78% | 70-78% |

TABLE B-continued

| Component | 1st Range | 2nd Range | 3rd Range |
|---|---|---|---|
| Disintegrant | 1-7% | 2-6% | 3-5% |
| Lubricant | 0.5-5% | 1-4% | 1-3% |
| Binder (Optional) | 0-10% | 0-8% | 0-6% |

In some aspects of the present disclosure, the tablet core comprises the components and concentration ranges in wt. % as indicated in Table C on the basis of a tablet containing 20 mg of the active drug.

TABLE C

| Component | 1st Range | 2nd Range | 3rd Range |
|---|---|---|---|
| Cobimetinib Hemifumarate Polymorph Form A | 17.5-18.5% | 17.5-18.5% | 17.5-18.5% |
| MCC | 36-47% | 39-47% | 42-47% |
| Lactose monohydrate | 24-31% | 26-31% | 38-47% |
| Croscarmellose sodium | 1-7% | 2-6% | 3-5% |
| Magnesium stearate | 0.5-5% | 1-4% | 1-3% |
| Binder (Optional) | 0-10% | 0-8% | 0-6% |

In some other aspects of the present disclosure, the tablet cores comprise the components and concentrations in wt. % as indicated in Table D on the basis of a tablet containing 20 mg of the active drug.

TABLE D

| Component | 1st Tablet | 2nd Tablet |
|---|---|---|
| Cobimetinib Hemifumarate polymorph Form A | 18.5% | 18.5% |
| MCC | 24.67% | 45.6% |
| Lactose monohydrate | 48.33% | 30.4% |
| Croscarmellose sodium | | |
| Intra-granular | 1% | 2% |
| Extra-granular | 1% | 2% |
| Magnesium stearate | | |
| Intra-granular | 0.375% | 0.25% |
| Extra-granular | 1.125% | 1.25% |
| Copovidone | 5% | 0% |

In some other aspects of the present disclosure, coated tablet cores comprise the components and concentrations in wt. % as indicated in Table E on the basis of a tablet containing 20 mg of the active drug. The components and concentrations in wt. % of a film coating composition are indicated in Table F.

TABLE E

| Component | 1st Tablet | 2nd Tablet |
|---|---|---|
| Cobimetinib Hemifumarate polymorph Form A | 17.96% | 17.79% |
| MCC | 23.95% | 43.85% |
| Lactose monohydrate | 46.92% | 29.23% |
| Croscarmellose sodium | | |
| Intra-granular | 0.97% | 1.92% |
| Extra-granular | 0.97% | 1.92% |
| Magnesium stearate | | |
| Intra-granular | 0.36% | 0.24% |
| Extra-granular | 1.09% | 1.21% |
| Copovidone | 4.85% | 0% |
| Film Coating | 2.91% | 3.85% |

TABLE F

| Component | Concentration |
|---|---|
| Polyvinyl Alcohol | 40% |
| Titanium Dioxide | 25% |
| Macrogol/PEG 3350 | 20.2% |
| Talc | 14.8% |

Methods of Treatment

Another aspect of this disclosure relates to methods of treating cancers comprising administering to a subject in need thereof the crystalline fumarate salt of Compound I. In a particular embodiment, the crystalline fumarate salt of Compound I is Form A. The amount of the crystalline fumarate salt of Compound I that is administered can be a therapeutically effective amount.

In another aspect of this disclosure, the method of treatment may be practiced by administering to a patient in need thereof a pharmaceutical composition comprising the crystalline fumarate salt of Compound I as discussed above and a pharmaceutically acceptable excipient. Another aspect of this disclosure relates to methods of treating cancers, as discussed above, where the cancer treated is melanoma (including BRAF V600 mutant melanoma), breast cancer (including triple negative breast cancer), colorectal cancer (including KRAS mutant colorectal cancer), non-small cell lung cancer, acute myeloid leukemia, and pancreatic cancer.

BRAF inhibitors have been used to treat melanoma, and vemurafenib is a BRAF inhibitor that is currently being used for treating melanoma. Thus, another aspect of this disclosure relates to a method of treating melanoma in a subject, the method comprising administering to the subject in need of the treatment a therapeutically effective amount of the crystalline fumarate salt of Compound I alone or in combination with vemurafenib. In one embodiment, the crystalline fumarate salt of Compound I is administered prior or subsequent to, or concurrent with vemurafenib. In another embodiment, the melanoma is BRAF V600 mutant melanoma. In a particular embodiment, the crystalline fumarate salt of Compound I is administered to a patient having unresectable or metastatic melanoma with BRAF V600 mutation. Another aspect of this disclosure relates to a method of treating BRAF V600 mutant melanoma in a subject, the method comprising administering to the subject in need of the treatment a therapeutically effective amount of the crystalline fumarate salt of Compound I alone or in combination with vemurafenib. In one embodiment, the crystalline fumarate salt of Compound I is administered prior or subsequent to, or concurrent with vemurafenib. In a particular embodiment, the crystalline fumarate salt of Compound I is administered in combination with Zelboraf® (vemurafenib) for the treatment of patients with unresectable or metastatic melanoma with BRAF V600 mutation.

Tyrosine kinase inhibitors have been used to treat non-small cell lung cancer (NSCLC). Gefitinib and erlotinib are angiogenesis inhibitors that target receptors of an epidermal growth factor called tyrosine kinase that are currently being used for treating NSCLC. Other compounds are in clinical development for the treatment of non-small cell lung cancer, as MEHD7945A. Thus, another aspect of this disclosure relates to a method of treating non-small cell lung cancer (NSCLC) in a subject, the method comprising administering to the subject in need of the treatment a therapeutically effective amount of the crystalline fumarate salt of Compound I, optionally in combination with erlotinib or gefitinib. In another embodiment, the combination is with erlotinib. In another embodiment, the combination is with MEHD7945A.

Another aspect of this disclosure relates to a method of treating diseases or disorders associated with uncontrolled, abnormal, and/or unwanted cellular activities comprising administering to a subject in need thereof a therapeutically effective amount of the crystalline fumarate salt of Compound I designated as Form A. This method of treatment may be practiced by administering a pharmaceutical composition of crystalline fumarate salt of Compound I designated as Form A.

Another aspect of this disclosure relates to a use of crystalline fumarate salt of Compound I designated as Form A according to any of the above embodiments for the manufacture of a medicament for the treatment of a disease or disorder discussed above. A pharmaceutical composition may be any pharmaceutical form which contains the crystalline fumarate salt of Compound I. The pharmaceutical composition may be, for example, a tablet, capsule, topical, or transdermal. The pharmaceutical compositions generally contain about 1% to about 99% by weight of the active compound(s), or a crystalline form of the active compound(s), and 99% to 1% by weight of one or more suitable pharmaceutical excipients. In one example, the composition will be between about 5% and about 75% by weight of active compound, with the rest being suitable pharmaceutical excipients, as discussed below.

A "therapeutically effective" amount of the crystalline fumarate salt of Compound I refers to an amount sufficient to treat a patient suffering from cancers. A therapeutically effective amount according to this disclosure is an amount therapeutically useful for the treatment or prevention of the disease states and disorders discussed herein. The crystalline fumarate salt of Compound I disclosed herein possesses therapeutic activity to inhibit, regulate and/or modulate the signal transduction of kinases, particularly, MEK 1/2 such as described in WO 2007/044515.

The actual amount required for treatment of any particular patient will depend upon a variety of factors including the disease state being treated and its severity; the specific pharmaceutical composition employed; the age, body weight, general health, sex and diet of the patient; the mode of administration; the time of administration; the route of administration; and the rate of excretion of the active compound(s), or a crystalline form of the active compound(s), according to this disclosure; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J.Hardman and L. Limbird, eds., McGraw-Hill Press, 155-173, 2001, which is incorporated herein by reference. The active compound(s), or a crystalline form of active compound(s), according to this disclosure and pharmaceutical compositions comprising them, may be used in combination with anticancer or other agents that are generally administered to a patient being treated for cancer. They may also be co-formulated with one or more of such agents in a single pharmaceutical composition.

Depending on the type of pharmaceutical composition, the pharmaceutically acceptable excipients may be chosen from any one or a combination of excipients known in the art. The choice of the pharmaceutically acceptable excipients depends partly upon the desired method of administration to be used. For a pharmaceutical composition of this disclosure, that is, one of the active compound(s), or a crystalline form of the active compound(s), of this disclosure, an excipient should be chosen so as to substantially maintain the particular form of the active compound(s), whether it would be crystalline or not. In other words, any excipients should not substantially alter the form of the active compound(s). Nor should the carrier be otherwise incompatible with the form of the active compound(s), such as by producing any undesirable biological effect or otherwise interacting in a deleterious manner with any other component(s) of the pharmaceutical composition.

The pharmaceutical compositions of this disclosure may be prepared by methods known in the pharmaceutical formulation art, for example, see Remington's Pharmaceutical Sciences, 18th Ed., (Mack Publishing Company, Easton, Pa., 1990). In solid dosage forms, Compound I is admixed with at least one pharmaceutically acceptable excipient such as sodium citrate or dicalcium phosphate or (a) other excipients such as fillers or extenders, as for example, starches, lactose, sucrose, glucose, mannitol, and silicic acid; (b) binders, as for example, cellulose derivatives, starch, alginates, gelatin, polyvinylpyrrolidone, sucrose, and gum acacia; (c) humectants, as for example, glycerol; (d) disintegrating agents, as for example, agar-agar, calcium carbonate, potato or tapioca starch, alginic acid, croscarmellose sodium, complex silicates, and sodium carbonate; (e) solution retarders, as for example paraffin; (f) absorption accelerators, as for example, quaternary ammonium compounds; (g) wetting agents, as for example, cetyl alcohol, and glycerol monostearate, magnesium stearate and the like; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable excipients, typically called adjuvants, known in the pharmaceutical formulation art may also be used in the pharmaceutical compositions of this disclosure. These include, but are not limited to, preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. If desired, a pharmaceutical composition of this disclosure may also contain minor amounts of auxiliary substances such as wetting or emulsifying agents, pH buffering agents, and antioxidants, such as, for example, citric acid, sorbitan monolaurate, triethanolamine oleate, and butylated hydroxytoluene.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the active compound(s), or a crystalline form of the active compound(s), with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Because the active compound(s), or a crystalline form of the active compound(s), is maintained during their preparation, solid dosage forms are preferred for the pharmaceutical composition of this disclosure. Solid dosage forms for oral administration, which includes capsules, tablets, pills, powders, and granules, are particularly preferred. In such solid dosage forms, the active compound(s) mixed with at least one inert, pharmaceutically acceptable excipient. Administration of the active compound(s), or a crystalline form of the active compound(s), in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. One preferable route of administration is oral administration, using a convenient dosage regimen that can be adjusted according to the degree of severity of the disease-state to be treated.

Preparation of (S)-[3,4-Difluoro-2-(2-fluoro-4-iodophenylamino)phenyl] [3-hydroxy-3-(piperidin-2-yl)azetidin-1-yl]-methanone (Compound I)

Compound I can be prepared as described in WO 2014/059422, the entire contents of which is hereby incorporated by reference, and as generally depicted in Scheme 1. Reaction of commercially available (3S,5R,8aS)-3-phenyl-hexahydro-oxazolo[3,2-a]pyridine-carbonitrile VII with commercially available tent-butyl-3-oxo-1-azetidinecarboxylate VIIa in the presence of base provides compound VI. Compound VI is treated with a hydride reducing agent such as sodium cyanoborohydride in the presence of acid, followed by treatment with aqueous sodium hydroxide, to provide compound V. Deprotection of V using acid gives compound IV, which is coupled to acid chloride IVa in the presence of a catalytic amount of pyridine to provide III. Hydrogenation of III provides piperidine derivative II. Finally, coupling of II with 2-fluoro-4-iodo aniline IIa provides the desired compound.

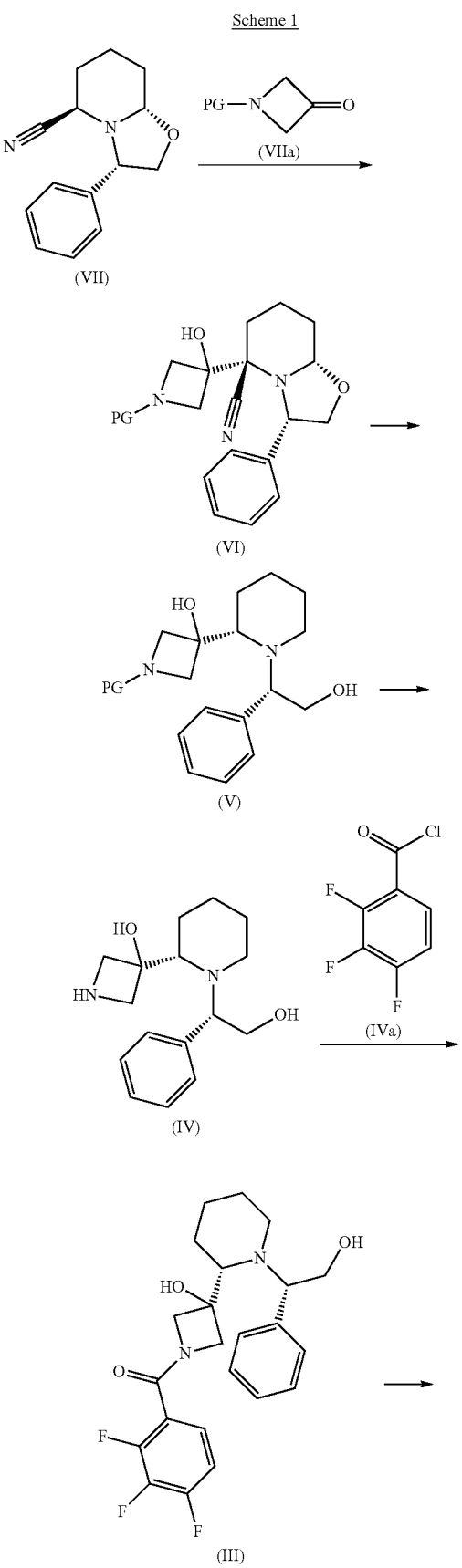

Scheme 1

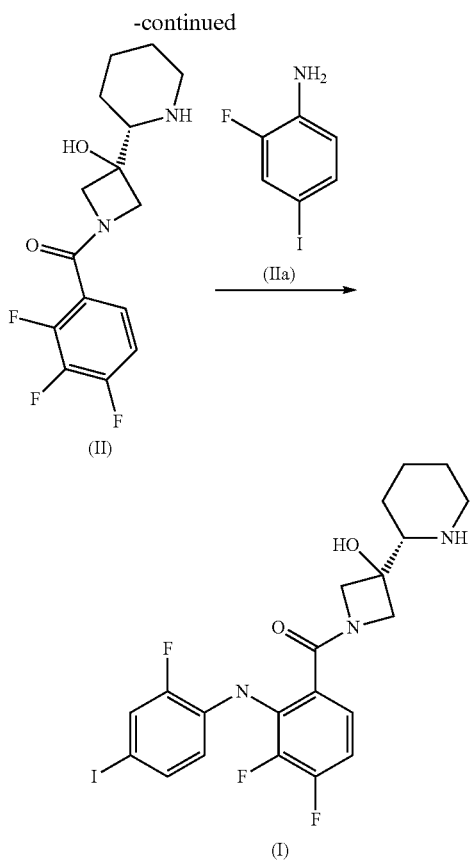

General Preparation Methods of Crystalline Forms

Crystalline forms may be prepared by a variety of methods including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline forms of a solvent mixture include, but are not limited to, for example, evaporation of the solvent; decreasing the temperature of the solvent mixture; crystal seeding of a supersaturated solvent mixture of the compound and/or salt thereof; crystal seeding a supersaturated solvent mixture of the compound and/or a salt from thereof; freeze drying the solvent mixture; and adding antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Ind. (1999).

In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the compound in the solution and precipitate the formation of crystals. An antisolvent is a solvent in which a compound has low solubility.

In one method that can be used in preparing crystals, the fumarate salt of Compound I can be suspended and/or stirred in a suitable solvent to afford a slurry, which may be heated to promote dissolution. The term "slurry," as used herein, means a saturated solution of the compound, wherein such solution may contain an additional amount of compound to afford a heterogeneous mixture of compound and solvent at a given temperature.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in "Programmed Cooling Batch Crystallizers," J. W. Mullin and J. Nyvlt, Chemical Engineering Science, 1971, 26, 3690377. In general, seeds of small size are needed to effectively control the growth of crystals in the batch. Seeds of small size may be generated by sieving, milling, or micronizing large crystals, or by microcrystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product washed with a suitable solvent, such as, for example, cold recrystallization solvent. After being washed, the product may be dried under a nitrogen purge to afford the desired crystalline form. The product may be analyzed by a suitable spectroscopic or analytical technique including, but not limited to, for example, differential scanning calorimetry (DSC); x-ray powder diffraction (XRPD); and thermogravimetric analysis (TGA) to assure the crystalline form of the compound has been formed. The resulting crystalline form may be produced in an amount greater than about 70 wt. % isolated yield, based on the weight of the compound originally employed in the crystallization procedure, and preferably greater than about 90 wt. % isolated yield. Optionally, the product may be delumped by being comilled or passed through mesh screen.

The features and advantages of this disclosure may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of this disclosure that are, for brevity reasons, described in the context of a single embodiment, may also be combined so as to form sub-combinations thereof. The disclosure is further illustrated by the following examples, which are not to be construed as limiting the disclosure in scope or spirit to the specific procedures described in them.

The definitions set forth herein take precedence over definitions set forth in any patent, patent application, and/or patent application publication incorporated herein by reference. All measurements are subject to experimental error and are within the spirit of the invention.

As used herein, "amorphous" refers to a solid form of a molecule and/or ion that is not crystalline. An amorphous solid does not display a definitive X-ray diffraction pattern with sharp maxima.

As used herein, the term "substantially pure" means Form A to contains at least about 90wt. % based on the weight of such crystalline form. The term "at least about 90 wt. %,"

while not intending to limit the applicability of the doctrine of equivalents to the scope of the claims, includes, but is not limited to, for example, about 90, about 91, about 92, about 93, about 94, about 95, about 96, about 97, about 98, about 99 and about 100% wt. %, based on the weight of the crystalline form referred to. The remainder of Form A may comprise other Form(s) of fumarate salt of Compound I and/or reaction impurities and/or processing impurities that arise, for example, when the crystalline form is prepared. The presence of reaction impurities and/or processing impurities may be determined by analytical techniques known in the art, such as, for example, chromatography, nuclear magnetic resonance spectroscopy, mass spectroscopy, and/or infrared spectroscopy.

In another aspect, the invention relates to a process for preparing the crystalline fumarate salt of Compound I designated as Form A, comprising:

adding fumaric acid dissolved in a solvent to a mixture of Compound I dissolved in a solvent to form the crystalline fumarate salt of Compound I designated as Form A; and collecting the resulting crystals of the crystalline fumarate salt of Compound I designated as Form A.

In this embodiment, the solvents that are employed are polar solvents. Depending on the solubility of fumaric acid and/or Compound I in a particular solvent, gentle heating (40-80° C.) may be necessary to ensure complete dissolution. For example, fumaric acid can be dissolved in a polar protic solvent such as an alcohol (for example, methanol, ethanol, n-propanol or isopropanol or the like), alone or as a mixture with one more other solvents or with water. Alternatively, fumaric acid can be dissolved in an aprotic solvent such as tetrahydrofuran, dichloromethane, or the like. Similarly, Compound I can be dissolved in dichloromethane or a polar solvent such as an alcohol (for example, methanol, ethanol, n-propanol or isopropanol or the like), alone or as a mixture with one or more other solvents or with water. The solution of fumaric acid is then added to the solution of Compound I and the resulting mixture is allowed to stand until a precipitate forms. In some instances, to expedite crystal formation, the resulting mixture is cooled or a seed crystal is added. In other instances, an anti-solvent such as a nonpolar hydrocarbon solvent such as heptane or the like is used to expedite crystal formation.

Thus, in another aspect, the invention relates to a process for preparing the crystalline fumarate salt of Compound I designated as Form A, comprising:

dissolving Compound I in a first solvent to form a first mixture;

dissolving fumaric acid in a second solvent to form a second mixture;

adding the first mixture to the second mixture with cooling to form the crystals as a precipitate; and collecting the crystals of the crystalline fumarate salt of Compound I designated as Form A.

As in the previous aspect, the solvents that are employed are polar solvents. In a particular embodiment, the first and second solvents are the same and are a mixture of isopropanol and water. In one embodiment, the ratio of isopropanol to water is 9:1. In another embodiment, the ratio of isopropanol to water is 4:1. In another embodiment, the ratio of isopropanol to water is 85:15. Typically, approximately 7 to 11 weight equivalents of the first solvent are used for every one weight equivalent of Compound I, and 2.0 to 3.0 weight equivalents of the second solvent are used for every one weight equivalent of fumaric acid. More particularly, approximately 8 to 10 weight equivalents of the first solvent are used for every one weight equivalent of Compound I, and 2.4 to 2.7 weight equivalents of the second solvent are used for every one weight equivalent of fumaric acid.

One molecule of fumaric acid forms a salt with two molecules of Compound I to form the hemifumarate salt of Compound I. Thus, about 0.5 equivalent of fumaric acid are used for every one equivalent of Compound I. Typically, 0.51 to 0.53 equivalent are used for every one equivalent of Compound I.

In a typical example, prior to the addition of the fumaric acid, Compound I dissolved in the first solvent is filtered, for instance, through activated carbon. Fumaric acid dissolved in the second solvent is then added slowly to the solution of Compound I in the first solution with gentle heating at a temperature of approximately 40-90° C.; more preferably 60-85° C.; and more preferably 75-80° C. In some instances, seeding crystals may be added to the mixture of Compound I and fumaric acid in the propanol/water solvent. To complete the crystallization process, the mixture can be cooled to approximately 20° C. The resulting crystals are isolated by filtration.

In a further aspect, the invention relates to a process for preparing the crystalline fumarate salt of Compound I designated as Form A, comprising:

adding fumaric acid dissolved in a solvent to a mixture of Compound I dissolved in a solvent to form the crystalline fumarate salt of Compound I designated as Form A as a precipitate.

In one embodiment of this aspect, the process further comprises adding seed crystals of the fumarate salt of Compound I designated as Form A to the mixture.

In an additional embodiment, the invention relates to a process for preparing the crystalline fumarate salt of Compound I designated as Form A, comprising dissolving the amorphous form of Compound I in a solvent with gentle heating at 65-80° C. and then allowing the resulting mixture to cool until crystals form. In one embodiment, seed crystals can be added to the mixture. In another embodiment, the mixture can be cooled to approximately 20° C. The resulting crystals are then isolated by filtration.

EMBODIMENTS

The invention is characterized by the following non-limiting embodiments.

Embodiment 1

A crystalline fumarate salt of (S)-[3,4-difluoro-2-(2-fluoro-4-iodophenylamino)phenyl] [3-hydroxy-3-(piperidin-2-yl) azetidin-1-yl]-methanone designated as Form A.

Embodiment 2

Figure 8:
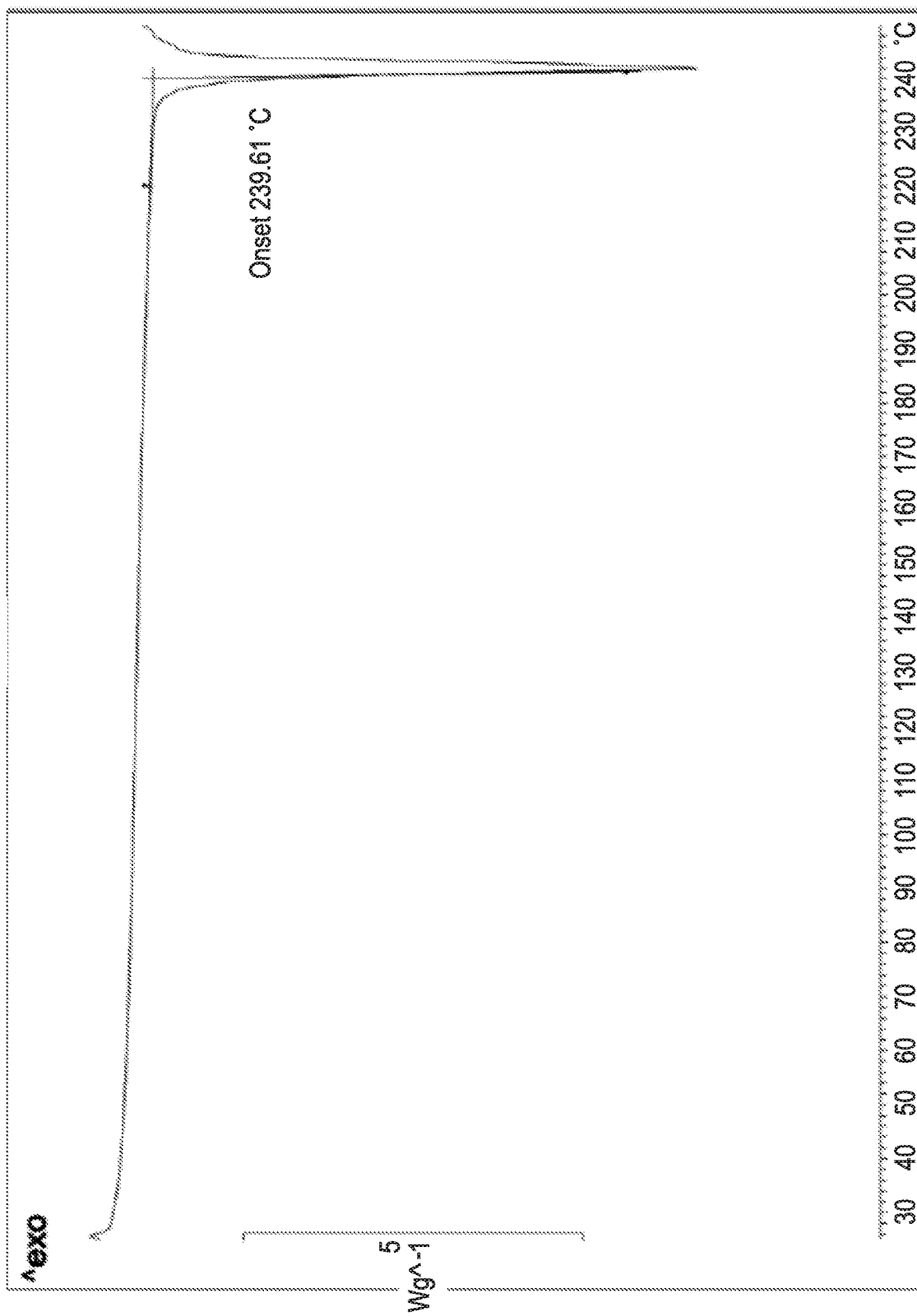
FIG. 8 shows the shows the differential scanning calorimetry trace for the crystalline fumarate salt of Compound I, designated as Form A.
Figure 10:
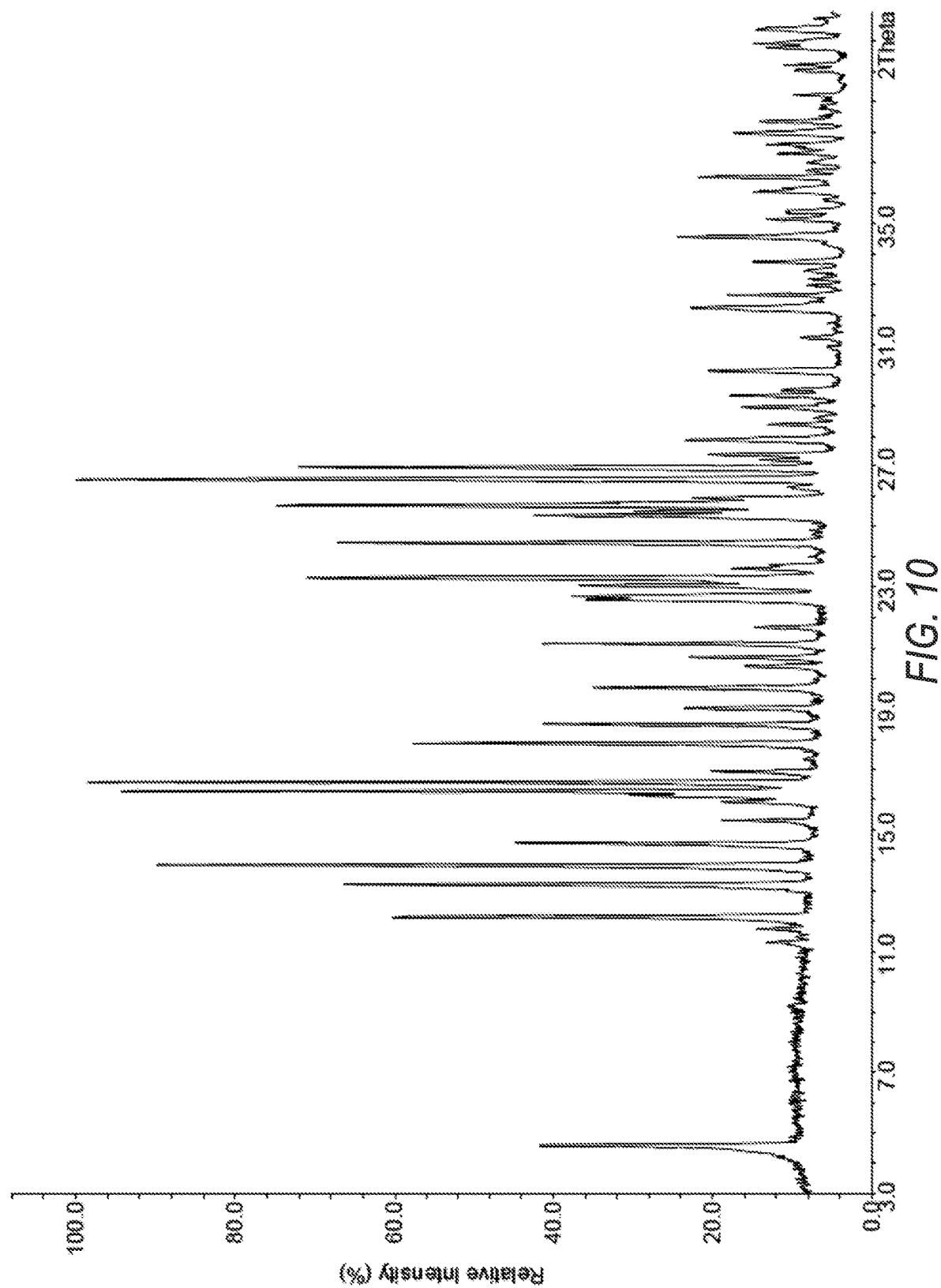
FIG. 10 shows the XRPD diffactogram for the crystalline fumarate salt of Compound I, designated as Form A.

The crystalline fumarate salt of (S)-[3,4-difluoro-2-(2-fluoro-4-iodophenylamino)phenyl] [3-hydroxy-3-(piperidin-2-yl) azetidin-1-yl]-methanone of Embodiment 1, designated as Form A, wherein said salt is characterized by at least one of the following:

(i) a $^1$H NMR spectrum in $d_6$ DMSO substantially as depicted in FIG. 2;

(ii) a 13C NMR spectrum in $d_6$ DMSO substantially as depicted in FIG. 3;

(iii) a solid state $^{13}$C NMR spectrum with three or more peaks selected from 175.3, 173.6, 117.5, 155.5, and 153.5, ± 0.2 ppm;

(iv) a solid state $^{13}$C NMR spectrum substantially as depicted in FIG. 4;

(v) a powder x-ray diffraction pattern (CuKα λ=1.5418 Å) comprising three or more 2θ values selected from 4.6, 12.1, 13.2, 13.6 and 14.5 ± 0.2 °2θ, wherein measurement of the crystalline form is at room temperature;

(vi) an x-ray powder diffraction (XRPD) pattern substantially in accordance with the pattern shown in FIG. 10; and (vii) a differential scanning calorimetry thermogram substantially in accordance with FIG. 8.

Embodiment 3

The crystalline fumarate salt of (S)-[3,4-difluoro-2-(2-fluoro-4-iodophenylamino)phenyl] [3-hydroxy-3-(piperidin-2-yl) azetidin-1-yl]-methanone of Embodiment 1, designated as Form A, wherein said salt is characterized by a solid state $^{13}C$ NMR spectrum with three or more peaks selected from 175.3, 173.6, 117.5, 155.5, and 153.5, ± 0.2 ppm.

Embodiment 4

The crystalline fumarate salt of (S)-[3,4-difluoro-2-(2-fluoro-4-iodophenylamino)phenyl] [3-hydroxy-3-(piperidin-2-yl) azetidin-1-yl]-methanone of Embodiment 1, designated as Form A, wherein said salt is characterized by a powder x-ray diffraction pattern (CuKα λ=1.5418 Å) comprising three or more 2θ values selected from 4.6, 12.1, 13.2, 13.6 and 14.5 ± 0.2 °2θ, wherein measurement of the crystalline form is at room temperature.

Embodiment 5

The crystalline fumarate salt of (S)-[3,4-difluoro-2-(2-fluoro-4-iodophenylamino)phenyl] [3-hydroxy-3-(piperidin-2-yl) azetidin-1-yl]-methanone of Embodiments 1-4, wherein said salt is least 90 weight % Form A, based on weight of said salt.

Embodiment 6

A pharmaceutical composition comprising crystalline fumarate salt of (S)-[3,4-difluoro-2-(2-fluoro-4-iodophenylamino)phenyl] [3-hydroxy-3-(piperidin-2-yl) azetidin-1-yl]-methanone of any one of Embodiments 1-3, designated as Form A; and a pharmaceutically acceptable excipient.

Embodiment 7

Use of crystalline fumarate salt of (S)-[3,4-difluoro-2-(2-fluoro-4-iodophenylamino)phenyl] [3-hydroxy-3-(piperidin-2-yl) azetidin-1-yl]-methanone of any one of Embodiments 1-5, designated as Form A, for the manufacture of a medicament for the treatment of cancer.

Embodiment 8

The crystalline fumarate salt of (S)-[3,4-difluoro-2-(2-fluoro-4-iodophenylamino)phenyl] [3-hydroxy-3-(piperidin-2-yl) azetidin-1-yl]-methanone of any one of Embodiments 1-5, designated as Form A, for use in therapy in treating cancer.

Embodiment 9

The crystalline fumarate salt of (S)-[3,4-difluoro-2-(2-fluoro-4-iodophenylamino)phenyl] [3-hydroxy-3-(piperidin-2-yl) azetidin-1-yl]-methanone designated as Form A, for use as a medicament for treating cancer which is selected from the group consisting of melanoma (including BRAF V600 mutant melanoma), breast cancer (including triple negative breast cancer), colorectal cancer (including KRAS mutant colorectal cancer), non-small cell lung cancer, acute myeloid leukemia, and pancreatic cancer.

Embodiment 10

The use of Embodiment 9, wherein the cancer is BRAF V600 mutant melanoma.

Embodiment 11

The crystalline fumarate salt of (S)-[3,4-difluoro-2-(2-fluoro-4-iodophenylamino)phenyl] [3-hydroxy-3-(piperidin-2-yl) azetidin-1-yl]-methanone designated as Form A, in combination with vemurafenib for use as a medicament for treating melanoma.

Embodiment 12

A method of treating BRAF V600 mutant melanoma in a subject, the method comprising administering to the subject in need of the treatment a therapeutically effective amount of the crystalline fumarate salt of Compound I alone or in combination with vemurafenib.

Embodiment 13

The method of Embodiment 12, wherein the crystalline fumarate salt of Compound I is administered prior or subsequent to, or concurrent with Vemurafenib.

Embodiment 14

A process for preparing the crystalline fumarate salt of Compound I designated as Form A, comprising adding fumaric acid dissolved in a solvent to a mixture of Compound I dissolved in a solvent to form the crystalline fumarate salt of Compound I.

The following examples illustrate the scope of the invention. The examples and preparations which follow are provided to allow those skilled in the art to more clearly understand and to practice the present invention. They should not be considered as limiting the scope of the invention, but merely as being illustrative and representative thereof

EXAMPLE 1

Synthesis of 3-((3S,5R,8aS)-5-Cyano-3-phenyl-hexahydro-oxazolo[3,2-a]pyridin-5-yl)-3-hydroxy-azetidine-1-carboxylic acid tert-butyl ester

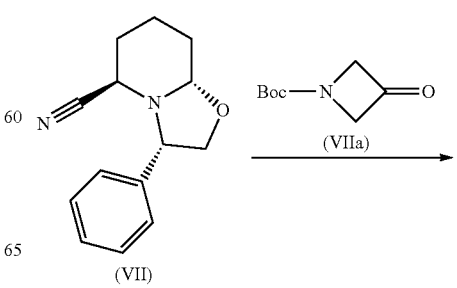

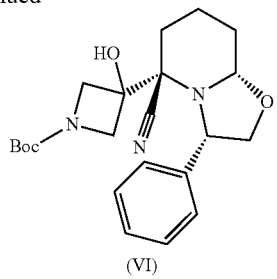

(VI)

A mixture of (3S,5R,8aS)-3-phenyl-hexahydro-oxazolo[3,2-a]pyridine-carbonitrile (20.0 g, 87.6 mmol, 1.0eq.) and dimethyltetrahydropyrimidone (DMPU, 11.3 g, 87.6 mmol, 1.0 eq.) in THF (95.1 mL) was stirred for 10 min until a clear solution was observed. The mixture was then cooled to −70 to −80° C. and lithium diisopropylamide (28% soln. in heptane, THF and ethylbenzene) (35.2 g, 92 mmol, 1.05 eq.) was added over 30 min while maintaining the internal temperature between −70 to −80° C. After complete addition, the mixture was stirred at −70 to −80° C. for an additional 2 h, followed by dosing a solution of 3-oxo-azetidine-1-carboxylic acid tert-butyl ester (16.2 g, 94.6 mmol, 1.08 eq.) in THF (16.4 g) over 30 min while maintaining the internal temperature between −70 to −80° C. After complete dosage, the reaction mixture was stirred at −70 to −80° c for 1 h.

In a separate flask, a solution of sodium chloride (10.3 g), deionized water (103.0 g) and acetic acid (5.29 g, 87.6 mmol, 1.0 eq.) was prepared and cooled to 0° C. The reaction mixture was dosed onto the quench mixture over 30 min while maintaining the internal temperature at less than 10° C. The flask of the reaction mixture was rinsed with THF (26.7 g) and the rinse was combined with the quenched mixture. After vigorously stirring for 20 min at 5° C., agitation was stopped and the layers were allowed to separate. The lower aqueous phase was discarded. Ethyl acetate (61.8 g) and deionized water (68.5 g) were added to the organic phase. After vigorously stirring at 5° C. for 10 min, agitation was stopped, the layers were allowed to separate, and the lower aqueous phase was discarded. The washing procedure was repeated once with deionized water (68.5 g).

The organic phase was concentrated under reduced pressure (jacket temperature approximately 40-45° C., pressure=200-180 mbar) until a total volume of approximately 120 mL of distillate was collected resulting in a yellowish solution. The vacuum was released and heptane (102.0 g) was added over 10 min. Distillation under reduced pressure was continued (jacket temperature approximately 35-40° C., pressure approximately 250-110 mbar) by adding heptane (177 g) at a rate so that the residual volume was kept constant. After 10 min of distilling, a thick, stirrable suspension was obtained. The vacuum was released and isopropanol (10.2 g) was added over 15 min at 35° C. The suspension was heated at 45° C. and stirred for 30 min. Thereafter, the suspension was cooled to 0° C. over 2 h and held at 0° C. for 1 h. The suspension was filtered over a glass filter. The flask and filter cake were rinsed with pre-cooled (approximately 5° C.) heptane (46.6 g), and the wet cake was dried overnight at 40° C. under reduced pressure until constant weight to yield the title compound as slightly beige crystals. HPLC purity: 91.9%-area. Mp. (DSC): extrapolated peak: 151.80° C.

$^1$H-NMR (600 MHz, CDCl$_3$): δ 7.30-7.50 (m, 5 H), 4.17-4.27 (m, 3 H), 3.94-4.01 (m, 2 H), 4.11-4.1 (m, 2 H), 4.09 (d, 1 H), 3.95 (d, 1 H), 3.87 (dd, 1 H), 3.76 (dd, 1 H), 3.54-3.70 (br, 1 H), 2.85-3.03 (br, 1 H), 2.18-2.25 (m, 1 H), 2.12 (br, 1 H), 1.97-2.04 (m, 1 H), 1.85-1.94 (m, 1 H), 1.61-1.79 (m, 3 H), 1.41 (s, 9 H). MS (EI): m/z=400.48 ([M+H]$^+$, 100%).

EXAMPLE 2

Synthesis of 3-Hydroxy-3-[(S)-1-((S)-2-hydroxy-1-pehyl-ethyl)-piperidin-2-yl] azetidine-1-carboxylic acid tert-butyl ester

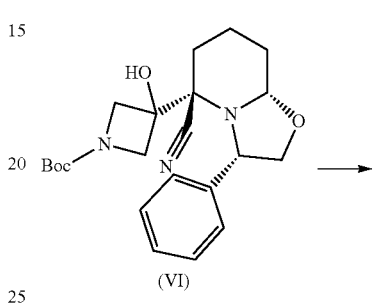

(VI)

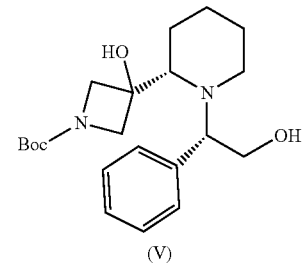

(V)

A mixture of 3-((3S, 5R, 8aS)-5-cyano-3-phenyl-hexahydro-oxazolo[3,2-a]pyridin-5-yl)-3-hydroxy-azetidine-1-carboxylic acid tert-butyl ester (12.0 g, 30.0 mmol, 1.0 eq.) and sodium cyanoborohydride (3.18 g, 50.6 mmol, 1.68 eq.) in EtOH (70 mL) was heated to 30° C. and slowly added within 2 h to a warm mixture (70° C.) of acetic acid (3.63 ml, 63.5 mmol, 2.1 eq.) in EtOH (20 mL). The resulting mixture was subsequently stirred for another 3 h at 70 to 75° C. After complete reaction, the mixture was cooled to 23° C. and slowly dosed within 30 min into a mixture of toluene (100 mL) and aqueous NaOH (60 g, 10%-w/w) and stirred for 15 min. The reaction flask was rinsed with the quenched mixture. The layers were separated, and the organic phase was washed with toluene (30 mL). The combined organic phases were concentrated under vacuum (200 to 85 mbar at 35 to 40° C. jacket temperature) until 80 mL (70.82 g) of a yellowish product solution was obtained. HPLC purity: 97.6% area.

For analytical purposes, the product solution was fully concentrated in the rotary evaporator, treated with EtOH and again fully concentrated resulting in 19.2 g of a foamy product. The residue was dissolved in a mixture of ethyl acetate (30 mL) and MeOH (15 mL) and purified by flash chromatography over 120 g silica gel using ethyl acetate as eluent. Fractions 3 to 5 of 6 fractions of 100 mL each were combined and fully concentrated under vacuum in the rotary evaporator resulting in 14.6 g of colorless foam. This residue was again dissolved in a minimum of a mixture of heptane/ ethyl acetate 2:1 (v/v) and purified by flash chromatography over 190 g of silica gel using heptane/ethyl acetate 2:1 (v/v) as eluent. After a forerun of 700 mL, ten subsequent fractions (800 mL total) were combined, fully evaporated in the rotary evaporator under vacuum (bath temperature 35° C., pressure >20 mbar) and the residue was dried overnight at 35° C. and under vacuum until constant weight to yield the title compound as a colorless solid. Mp. (DSC): extrapolated peak: 220.9° C. (melting accompanied by exothermic decomposition).

$^1$H-NMR (600 MHz, CDCl$_3$): δ 7.38-7.41 (m, 2 H), 7.34-7.38 (m, 2 H), 7.27-7.30 (m, 1 H), 4.28-4.50 (br, 1 H), 4.19 (dd, 1 H), 4.11-4.1 (m, 2 H), 4.09 (d, 1 H), 3.95 (d, 1 H), 3.87 (dd, 1 H), 3.83 (t, 1 H), 3.08-3.16 (m, 1 H), 2.85 (ddd, 1 H), 2.57 (ddd, 1 H), 1.76-1.84 (m, 1 H), 1.68-1.75 (m, 1 H), 1.53-1.58 (m, 1 H), 1.41-1.48 (bs, 9 H), 1.31-1.41 (m, 2 H), 1.21-1.31 (m, 2 H). MS (EI): m/z=377.24 ([M+H]$^+$, 100%). EA for C$_{21}$H$_{32}$N$_2$O$_4$: calcd: C 66.99, H 8.57, N 7.44; found C 67.38, H 8.50, N 7.29.

EXAMPLE 3

Synthesis of 3-[(S)-1-((S)-2-Hydroxy-1-phenyl-ethyl)-piperidin-2-yl]-azetidin-3-ol di hydrochloride

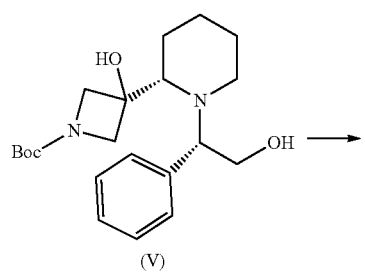

(V)

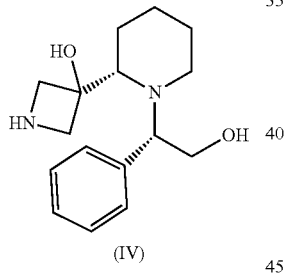

(IV)

A solution of 3-hydroxy-3-[((S)-1-((S)-2-hydroxy-1-phenyl-ethyl)-piperidin-2-yl]azetidine-1-carboxylic acid tert-butyl ester (69.8 g, 29.6 mmol, 1.0 eq.) in toluene was treated at 23-27° C. within 12 min with a mixture of water (30.1 g) and HCl (37%, 7.22 g, 73.3 mmol, 2.5 eq.) and stirred for 10 min. The resulting biphasic mixture was heated to 50° C. within 30 min and kept stirring for 4 h at 50° C. After complete conversion, the mixture was cooled down to room temperature and the phases were allowed to separate. The aqueous phase was washed with toluene (36 mL) and the phases were allowed to separate, resulting in 44.2 g of a yellowish aqueous product solution. HPLC purity: 96.3%-area.

For analytical purposes, the product solution was fully concentrated in the rotary evaporator (bath temperature 45° C.). The yellow oily residue was dissolved in MeOH (190 mL) and again fully concentrated in the rotary evaporator and under vacuum. The residue was taken up in a minimum of a mixture of MeOH/ethyl acetate 1:1 (v/v) and purified by flash chromatography over silica gel (150 g) using a mixture of MeOH/ethyl acetate 1:1 (v/v) as eluent. A forerun of 400 mL was taken and discarded and the subsequent fractions (1.5 L) were combined and completely concentrated in the rotary evaporator under vacuum (bath temperature 40° C., pressure >20 mbar) resulting in a yellow oil that was dissolved in MeOH (20 mL). The oil was added drop-wise at room temperature to ethyl acetate (80 mL), whereupon the product precipitated. The solids were filtered and rinsed with ethyl acetate (30 mL). Drying overnight at 30° C. under vacuum until constant weight resulted in the title compound (22.0 g) as a colorless solid. Mp. (DSC): T$_{onset}$ 114.2° C., extrapolated peak: 123.4° C.

$^1$H NMR (600 MHz, DMSO-d$_6$): δ 9.50-9.64 (br, 1 H), 8.91-9.03 (br, 1 H), 7.78 (s, 1 H), 7.62-7.56 (m, 2 H), 7.41-7.52 (m, 3 H), 6.03 (bs, 1 H), 4.56-4.67 (m, 1 H), 4.45 (dd, 1 H), 4.25-4.33 (m, 2 H), 4.23 (dd, 1 H), 4.18 (dd, 1 H), 3.95-4.05 (m, 1 H), 3.83 (dd, 1 H), 3.45-3.54 (m, 1 H), 3.26-3.40 (m, 1 H), 1.67-1.86 (m, 4 H), 1.55-1.65 (m, 1 H), 1.37-1.51 (m, 1 H). MS (EI): m/z=277 ([M+H]$^+$ of free base, 100%). EA for C$_{16}$H$_{26}$N$_2$O$_2$Cl$_2$, corrected for water (9.2%-w/w) and HCl (2.1 eq. instead of 2.0 eq.): calcd: C 49.44, H 7.80, N 7.21, O 16.40, Cl 19.15; found C 48.76, H 7.48, N 7.36, O 16.44, Cl 19.11.

EXAMPLE 4

{3-Hydroxy-3-[(S)-1-((S)-2-hydroxy-1-phenyl-ethyl)-piperidin-2-yl]-azetidin-1-yl}-(2,3,4-trifluoro-phenyl)-methanone

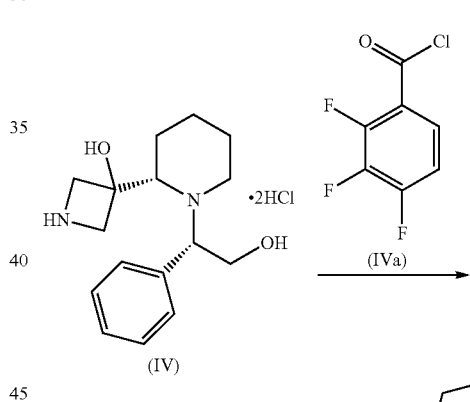

(III)

2,3,4-Trifluoro-benzoyl chloride:

2,3,4-Trifluorobenzoic acid (100 g, 568 mmol, 1.0 eq.) was suspended in toluene (1000 mL) and treated with pyridine (0.254 mL, 3.15 mmol, 0.0055 eq.). The resulting suspension was heated to 60 to 70° C., whereupon the mixture became a clear yellowish solution. At this temperature, oxalyl chloride (94.4 g, 729 mmol, 1.3 eq.) was slowly added over 156 minutes. After complete addition, the mixture was kept stirring for 10 min until complete. Toluene (360 mL) was partially removed by distillation under vacuum (jacket temperature: 60 to 70° C., pressure: 200 to 100 mbar). The solution was cooled to room temperature, resulting in 636 g of a yellowish and slightly turbid solution that was stored under $N_2$ atmosphere and used in the subsequent step without any further treatment. HPLC purity: 99.2%-area.

{3-Hydroxy-3-[(S)-1-((S)-2-hydroxy-1-phenyl-ethyl)-piperidin-2-yl]-azetidin-1-yl}-(2,3,4-trifluoro-phenyl)-methanone:

The aqueous solution of 3-[(S)-1-((S)-2-hydroxy-1-phenyl-ethyl)-piperidin-2-yl]-azetidin-3-ol di hydrochloride (43.5 g) was treated with EtOH (24 mL) and stirred for 10 min at room temperature. To this mixture was added a solution of tripotassium phosphate (28.8 g, 136 mmol, 4.7 eq.) in 261 mL water within 14 min at a batch temperature of 10 to 20° C. and the mixture was stirred for 15 min at 15° C. (pH 11.9). To this solution was added via dropping funnel 34 g of the above described 2,3,4-Trifluoro-benzoyl chloride solution (34.0 g, 29.8 mmol, 1.0 eq.) over 32 min at a batch temperature of 10 to 20° C. while vigorously stirring. The dropping funnel was rinsed with toluene (1.2 ml) and the biphasic mixture was stirred at room temperature for 60 min. The layers were allowed to separate, and the aqueous phase was discarded. The organic phase was washed with a solution of sodium carbonate (3.36 g, 31.5 mmol, 1.09 eq.) in water (42 g) and stirred for 30 min at room temperature. The layers were allowed to separate, and the organic phase was washed with aqueous sodium chloride (30 g, 10%-w/w). In the rotary evaporator (bath temperature 50° C., pressure <200 mbar), the organic phase was concentrated to a volume of approximately 30%. The residue was taken up in EtOH (23 mL) and stirred for 5 min at 40 to 50° C. The solution was again concentrated in the rotary evaporator (bath temperature 50° C., pressure less than 200 mbar, 17 ml distillate), resulting in a very viscous oil. The residue was again taken up in EtOH (23 mL) and stirred for 10 min and again further diluted with EtOH (12 mL) in order to reach the target volume (53 mL, 46.06 g). HPLC purity: 85.0%-area.

For analytical purposes, the product solution (90 mL) was filtered and the filter residue was washed with EtOH (15 ml). In the rotary evaporator (bath temperature 40° C., pressure <150 mbar), the solution was completely concentrated, and the residue was taken up in MTBE (40 mL), subsequently again fully concentrated, then taken up in a mixture of ethyl acetate (29 mL) and heptane (40 mL), then fully concentrated, then again taken up in a mixture of MTBE (20 mL) and heptane (50 mL) and again fully concentrated resulting, finally, in a foamy solid (32.5 g). The solid residue (32.0 g) was dissolved in ethyl acetate (20 mL) and purified by flash chromatography over silica gel (150 g) using ethyl acetate as eluent. After a forerun of 200 mL, 6 fractions (800 mL) were combined and completely concentrated in the rotary evaporator (bath temperature: 40° C., pressure >20mbar) resulting in 28.0 g of a slightly yellowish oil. At room temperature, the oily residue was taken up in dichloromethane (20 mL), diluted with heptane (150 mL) and again fully concentrated in the rotary evaporator, followed by dissolving the residue in MTBE (20 mL) and again by complete removal of the solvent in the rotary evaporator resulting in a rubber-like foam. This foam was dissolved in toluene (30 mL, room temperature) and dosed over 20 min added drop-wise by dropping funnel at room temperature to heptane (400 mL), whereupon the product started to precipitate. The dropping funnel was rinsed with toluene (4 mL) and the suspension was kept stirring for 1 h at room temperature. The solids were filtered off and the reactor and filter cake were twice rinsed with the filtrate and subsequently with heptane (15 mL). Drying under vacuum at 35° C. until weight constancy resulted in 17.88 g of a colorless solid. HPLC purity: 97.0%-area, residual solvents: toluene (1.2%-w/w) and heptane (2.3%-w/w). Mp (visually): $T_{onset}$: 55-73° C. (melting accompanied by exothermic decomposition).

$^1$H NMR (400 MHz, DMSO-$d_6$, 120° C.): δ 7.41-7.47 (m, 2 H), 7.27-7.32 (m, 2 H), 7.21-7.26 (m, 2 H), 7.12-7.19 (m, 1 H), 5.21 (bs, 1 H), 4.35 (bd, 1 H), 4.22 (bs, 1 H), 4.05 (dd, 1 H), 3.91-4.01 (m, 1 H), 3.74-3.90 (m, 4 H), 3.01 (dd, 1 H), 2.75-2.84 (m, 1 H), 2.49-2.59 (m, 1 H), 1.68-1.81 (m, 1 H), 1.51-1.65 (m, 1 H), 1.23-1.50 (m, 3 H), 1.09-1.22 (m, 1 H). MS (EI): m/z=435 ([M+H]$^+$, 100%). EA for $C_{23}H_{25}F_3N_2O_3$, corrected for residual toluene (1.2%-w/w) and heptane (2.3%-w/w): calcd: C 64.38, H 6.07, F 12.66, N 6.22; found C 64.01, H 6.04, F 12.63, N 6.35.

EXAMPLE 5

Synthesis of ((S)-3-Hydroxy-3-piperidin-2-yl-azetidin-1-yl)-(2,3,4-trifluoro-phenyl)-methanone hydrochloride

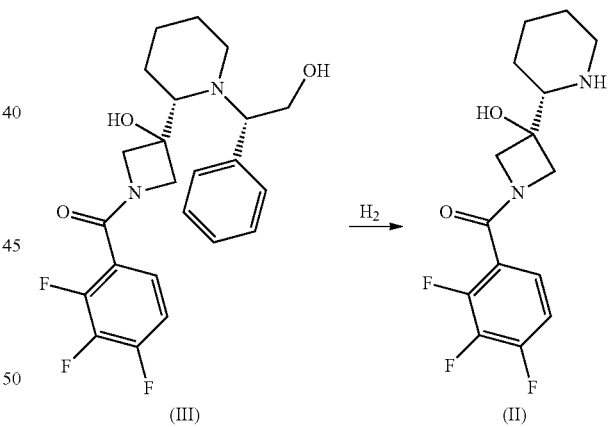

A 185 mL glass autoclave under argon was charged with Pd/C (3.37 g, 1.3 mmol, 0.04 eq, 60.2% ww water, 10% ww Pd on C), water (0.22 g) and a solution of {3-hydroxy-3-[(S)-1-((S)-2-hydroxy-1-phenyl-ethyl)-piperidin-2-yl]-azetidin-1-yl}-(2,3,4-trifluoro-phenyl)-methanone in EtOH (53 mL, 46 g, 29 mmol, 1.0 eq.). The mixture was treated with EtOH (13 mL), Acetic acid (4.15 mL, 72 mmol, 2.5 eq.) and with aqueous hydrochloric acid (2.5 ml, 37%-w/w, 30 mmol, 1.0 eq.). The autoclave was rendered inert, pressurized with 2 bar of $H_2$, and the reaction was run at 2 bar $H_2$ pressure at 25° C. for 12 h. The pressure was released from the autoclave, and the suspension was treated with MeOH (25 mL) and kept stirring for 30 min and filtered under argon protection over filter paper. The autoclave and the filter residue were rinsed with MeOH (4 mL). The combined filtrates were evaporated under reduced pressure to approximately 20-30 percent of the initial volume. The residue was treated with isopropanol (38.5 mL) at 30 to 35° C., stirred for 1 h, cooled to 20 to 25° C., and treated with water (0.58 g) and with aqueous hydrochloric acid (2.5 mL, 37%-ww, 30 mmol, 1.0 eq.). The resulting suspension was concentrated under vacuum at 25 to 35° C. until a volume of approximately 22 mL was reached, and MTBE (31 mL) was added at 25 to 35° C. The final suspension was cooled to 5 to 10° C., stirred for 1 h, and then filtered. The filter cake was rinsed with cold MTBE (12 mL) and dried under vacuum at 35° C. until weight constancy to yield the title compound (5.08 g) as a colorless solid. HPLC purity: 99.6%-area. Mp. (DSC): $T_{onset}$: 246.3° C., extrapolated peak: 248.8° C. (melting accompanied by exothermic decomposition).

$^1$H NMR (400 MHz, DMSO-$d_6$, 120° C.): δ 8.59 (bs, 2 H), 7.14-7.48 (m, 2 H), 6.54 (bs, 1 H), 4.39 (dd, 1 H), 4.23 (dd, 1 H), 3.85-3.97 (m, 2 H), 3.27-3.35 (m, 1H), 3.20-3.27 (m, 1 H), 2.80-2.95 (m, 1 H), 1.78-1.88 (m, 2 H), 1.64-1.78 (m, 2 H), 1.40-1.64 (m, 2 H). MS (EI): m/z=315 ([M+H]$^+$ of free base, 100%). EA for $C_{15}H_{17}F_3N_2O_2$ x HCl: calcd: C 51.36, H 5.17, N 7.99, F 16.25; found C 51.19, H 4.89, N 7.91, F 16.06.

EXAMPLE 6

Synthesis of (S)-[3,4-difluoro-2-(2-fluoro-4-iodo-phenylamino)phenyl] [3-hydroxy-3-(piperidin-2-yl) azetidin-1-yl]-methanone (Compound I)

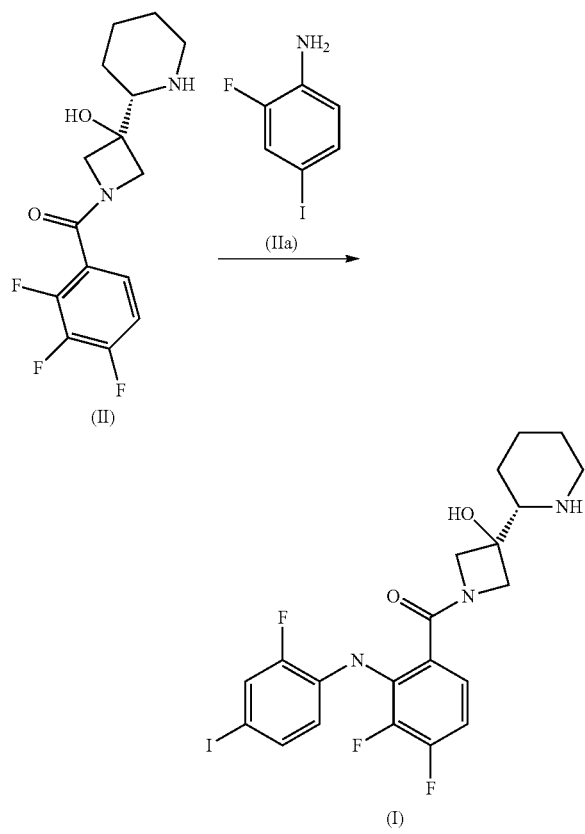

To a solution of ((S)-3-hydroxy-3-piperidin-2-yl-azetidinb 1-yl)-(2,3,4-trifluoro-phenyl)-methanone hydrochloride (15.0 g,42.8 mmol, 1.0 eq.) and 2-flouro-4-iodo-anilin (11.1 g, 47 mmol, 1.1 eq.) in THF (90 ml), a solution of LiHMDS in THF (149 g, 20.7% w/w, 184 mmol, 4.3 eq.) was dosed over 88 min at 20 to 30° C. Stirring was continued for 2 h. After complete conversion, the mixture was dosed to a mixture of sulfuric acid (12.0 g, 96%-w/w, 118 mmol, 2.75 eq.) in water (75 mL) over 25 min and kept stirring for 1 h. The layers were allowed to separate, and the organic phase was washed with a mixture of water (60 mL) and toluene (96 mL). The organic phase was concentrated under vacuum to a volume of approximately 150 mL. Toluene (250 mL) was added and residual THF was removed by distillation at 55° C. jacket temperature and at a pressure of 84 mbar while keeping the batch volume constant by continuous dosing of toluene (400 mL), resulting in slow precipitation of the product. The batch temperature was then lowered to 10° C. within 2 h, and the suspension was kept stirring overnight at 10° C. The product was filtered off, and the cake was rinsed with cold toluene (150 mL). Drying overnight under vacuum at 35° C. until weight constancy yielded the title compound (20.66 g) as a colorless product. HPLC purity: 99.7%-area. M.p (DSC): $T_{onset}$: 166.7° C., extrapolated peak: 168.2° C. (91.5 J/g). $^1$H NMR (600 MHz, CDl$_3$): δ 8.28-8.48 (br, 1 H), 7.39 (dd, 1 H), 7.32 (ddd, 1 H), 7.09-7.14 (m, 1 H), 6.75-6.86 (br, 1 H), 6.60 (ddd, 1 H), 4.10 (d, 2 H), 4.05-4.20 (br, 1 H), 3.93-4.04 (br, 1 H), 3.09 (d, 1 H), 2.70 (d, 1 H), 2.56-2.67 (br, 1 H), 1.68-1.87 (m, 1 H), 1.50-1.64 (m, 2 H), 1.25-1.38 (m, 2 H), 1.07-1.24 (m, 1 H). MS (EI): m/z=532 ([M+H]$^+$, 100%). EA for $C_{21}H_{21}F_3O_2O_3$: calcd: C 47.47, H 3.98, N 7.91, F 10.73; found C 47.68, H 4.00, N 7.66, F 10.80.

EXAMPLE 7

Preparation of the Crystalline Fumarate Salt of (S)-[3,4-difluoro-2-(2-fluoro-4-iodophenylamino)phenyl] [3-hydroxy-3-(piperidin-2-yl) azetidin-1-yl]-methasone (Compound I) Designated as Form A (S)[3,4-Difluoro-2-(2-fluoro-4-iodophenylamino)phenyl] [3-hydroxy-3-(piperidin-2-yl) azetidin-1-yl]-methanone (80 kg) was dissolved in a mixture of 2-propanol/water 88:12 w/w (9 weight equivalents (weq)) at 77° C. and filtered over activated carbon. Fumaric acid (0.52 eq.) was dissolved in a mixture of 2-propanol/water 88:12 w/w (2.6 weq). An initial amount of the fumaric acid solution (8% of the overall amount) was added to the filtered solution of (S)-[3,4-difluoro-2-(2-fluoro-4-iodophenylamino)phenyl] [3-hydroxy-3-(piperidin-2-yl) azetidin-1-yl]-methanone at 77° C. Seeding crystals (0.023 weq) were added as a suspension in a mixture of 2-propanol/water 88:12 w/w (0.2 weq) at 77° C. The remaining amount of the fumaric acid solution was added within 6 hours at the same temperature. To complete crystallization, the suspension was cooled to 20° C. within 7 hours. The fumarate salt crystalline Compound I Form A was isolated by centrifugation, washed with 2-propanol (e.g., 0.6 weq.), dried under reduced pressure at max. 55° C. and delumped.

Characterization Examples for Crystalline Fumarate Salt of (S)-[3,4-difluoro-2-(2-fluoro-4-iodophenylamino)phenyl] [3-hydroxy-3-(piperidin-2-yl) azetidin-1-yl]-methanone Designated as Form A

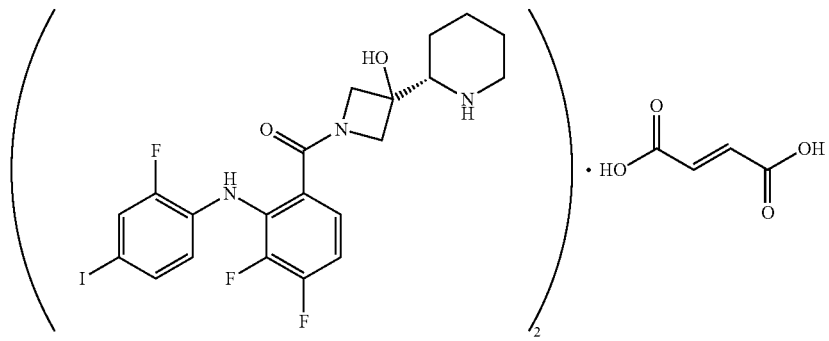

Elemental Analysis

The elemental analysis results were calculated from a relative molecular mass of 1178.71 g/mol and a composition of $C_{46}H_{46}F_6I_2N_6O_8$ and are shown in Table 1. The results are consistent with structure depicted above.

TABLE 1

Elemental Analysis of $C_{46}H_{46}F_6I_2N_6O_8$

| Element | Calculated | Found |
| --- | --- | --- |
| C | 46.87% | 46.76% |
| H | 3.93% | 3.95% |
| N | 7.13% | 7.07% |
| F | 9.67% | 9.63% |
| I | 21.53% | 21.57% |
| O | 10.86% | 10.84% |

Infrared Spectroscopy

Figure 1:
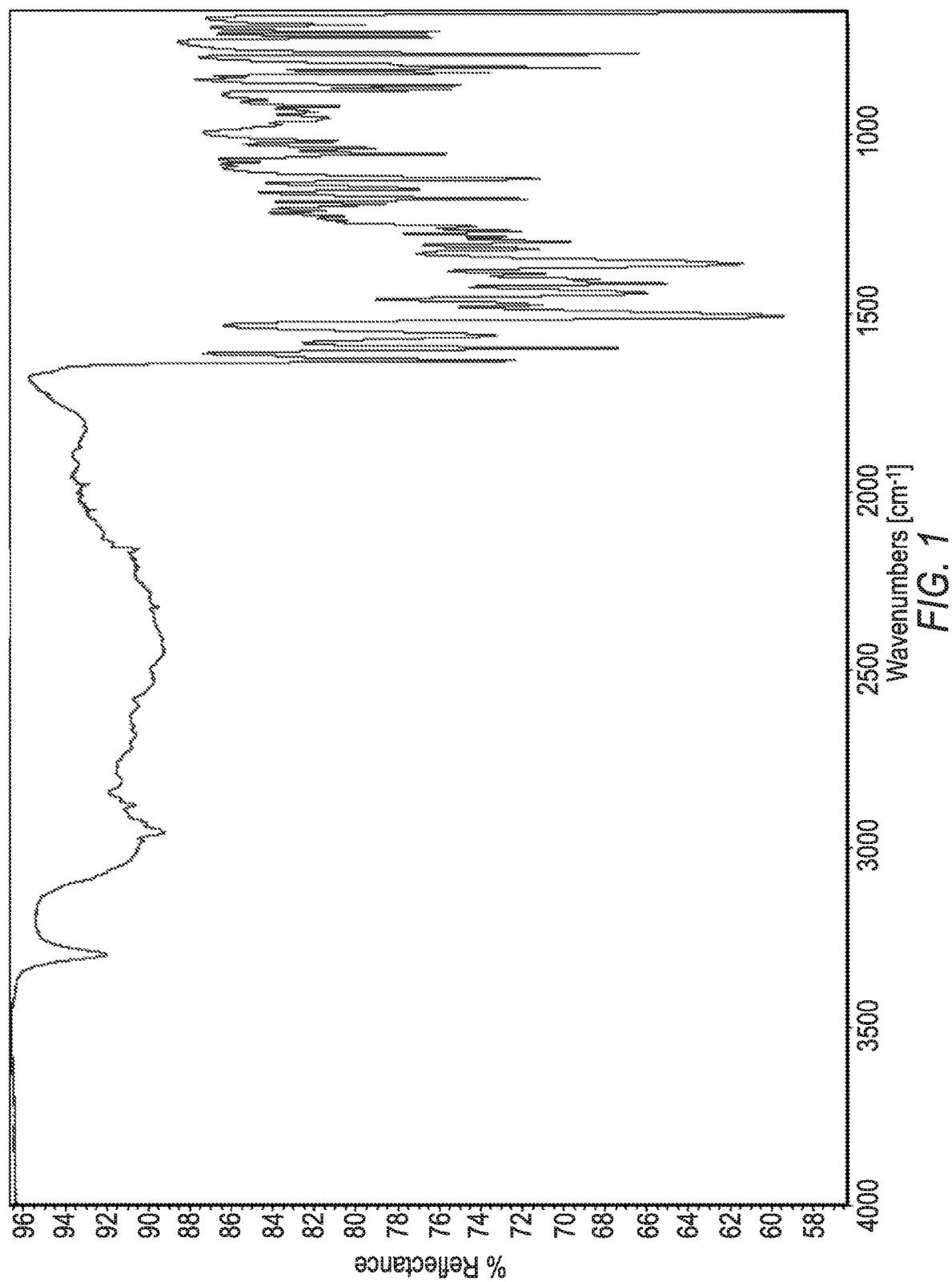
FIG. 1 shows the infrared spectrum of the crystalline fumarate salt of Compound I, designated as Form A.

A ThermoScientific iS5 Fourier transform infrared (FTIR) spectrophotometer with iD5 ATR accessory was used. The infrared (IR) spectrum was recorded as reflection IR measurement in the range of 4000-650 cm$^{-1}$ and is provided as FIG. 1. The IR spectrum is consistent with the structure depicted above. A summary of characteristic IR stretches is provided in Table 2.

TABLE 2

IR Assignments for Fumarate Salt of Compound I

| Wavenumber (cm$^{-1}$) | Assignment |
| --- | --- |
| 3500-2800 | OH stretch (broad) |
| 3296 | NH stretch |
| 2978, 2957, 2879 | Alkyl CH stretch |
| 2700-2300 | NH2 + stretch |
| 1632 | C = stretch amide I |
| 1598, 1563 | Aromatic ring: breathing vibration and NH2 + bending |
| 1508 | Aromatic ring: breathing vibration |
| 1443 | Alkyl CH bending |
| 1416 | OH deformation |
| 1319 | Alkyl CH bending |
| 1361, 1299, 1270, 1180, 1152, 1122 | Carboxylic acid OH deformation and C—O stretching vibration, N—C=O bending vibration, Aryl-F stretch |

TABLE 2-continued

IR Assignments for Fumarate Salt of Compound I

| Wavenumber (cm$^{-1}$) | Assignment |
| --- | --- |
| 1054 | Aryl-I stretch |
| 862, 825, 773, 725 | Out of plane CH vibration aromatic rings |

NMR Spectra in Dimethyl Sulfoxide Solution

Nuclear magnetic resonance (NMR) measurements were carried out on Bruker Avance 600 and 400 MHz spectrometers. The 600 MHz machine was equipped with a 5 mm, TCI, z-gradient CryoProbe and the 400 MHz machine was equipped with a 5 mm, BBFO, z-gradient Probe. The sample was prepared by dissolving 6 mg of the crystalline fumarate salt of Compound I designated as Form A in 0.75 mL DMSO-d6 (D, 99.8%) for all proton detected experiments. For $^{13}$C-NMR and $^{19}$F-NMR, 62 mg were dissolved in 0.75 mL DMSO-d6.

$^1$H-NMR (600 MHz, DMSO-d6 at 25° C.): The $^1$H-NMR spectrum at 600 MHz at 25° C. showed a 2:1 relation of free base and fumarate taking the integral of the signals at 6.62 and 6.42 ppm, proving the existence of a hemifumarate. There were eight proton signals for the azetidine ring, whereas only four were expected, indicating the existence of two signal sets in a 1:1 ratio.

The $^1$H NMR (d6 DMSO) is depicted in FIG. 2. δ 8.54 (s, 1H) 8.50 (s, 1H), 7.57 (dd, 2H), 7.37 (dd, 2H), 7.31 (m, 2H), 7.18 (m, 2H), 6.67 (t, 2H), 6.42 (s, 2H), 4.25 (d, lH), 4.15 d, 1H), 4.09 (d, 1H) 4.01 (d, 1H), 3.92 (d, 1H), 3.86 (d, 1H), 3.71 (t, 2H) 3.03 (d, 2H), 2.79 (m, 2H) 8, 38 (t, 2H), 1.62 (m, 6H) 1.24 (m 6H) (2.50 quint 1.9 DMSO).

The $^{13}$C NMR (d6 DMSO) is depicted in FIG. 3. δ 168.0, 167.5, 152.3, 151.4, 143.6, 135.2, 133.2, 131.3, 130.5, 124.6, 123.7, 123.0, 122.7, 119.8, 119.6, 110.7, 81.6, 81.5, 70.3, 70.3, 63.0, 61.8, 60.7, 60.6, 59.0, 58.1, 45.5, 45.4, 24.1, 23.7, 23.1, 39.5 (DMSO-d6).

To support the results from liquid-state NMR spectroscopy, solid-state NMR spectroscopy was also performed for elucidation of structure. In liquid-state NMR spectroscopy, some of the signals are doubled due to the observed restrictions in free rotation leading to a rotameric mixture, whereas the result of solid-state NMR spectroscopy is not influenced by this sterical hindrance. Therefore, a more unambiguous peak assignment is possible for the fumarate salt of Compound I using solid-state NMR spectroscopy.

The $^{13}$C solid-state NMR of Form A is depicted in FIG. 4. δ 175.3, 173.6, 168.9, 155.5, 153.5, 144.4, 142.5, 137.0, 136.0 135.5, 132.0, 130.5, 127.2, 125.0, 124.0, 117.9m 108.0, 82.2, 71.7, 64.0, 59.3, 56.2, 45.0, 25.3, 24.0, 22.2.

The $^{13}$C solid-state NMR of Form A confirms the results from other analytical technologies used to elucidate the structure of (S)-[3,4-Difluoro-2-(2-fluoro-4-iodophenylamino)phenyl] [3-hydroxy-3-(piperidin-2-yl) azetidin-1-yl] methanone. All carbons present in the structure of the free base as well as in the structure of the counterion are detected in the spectra.

$^{19}$F-NMR (600 MHz, DMSO-d6 at 25° C.): The 19-F NMR showed three different fluorine atoms.

Mass Spectrometry

Figure 5:
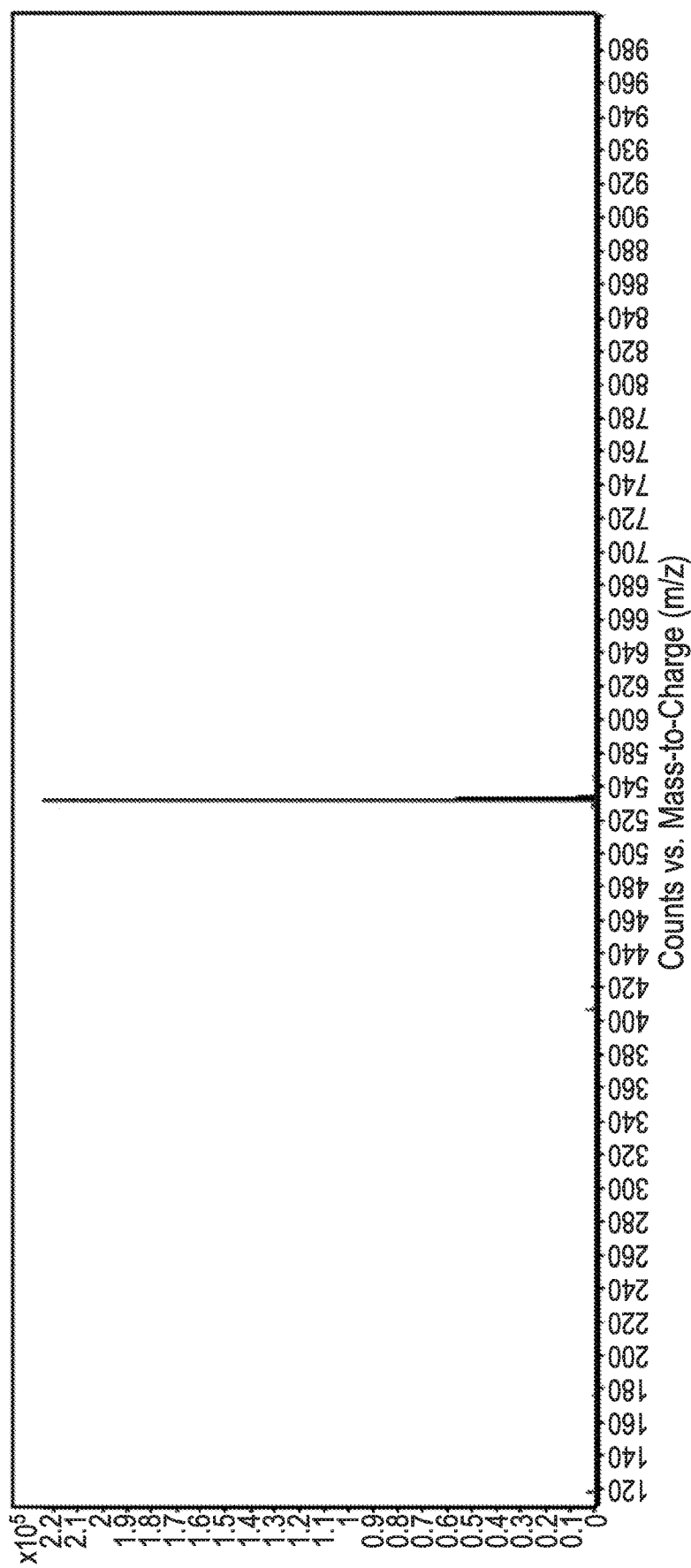
FIG. 5 shows the positive electrospray mass spectrum for the crystalline fumarate salt of Compound I, designated as Form A.

An Agilent 6520 QTOF spectrometer was used for ESI positive CID MSMS and ESI negative MS. The positive electrospray mass spectrum obtained for the fumarate salt of Compound I is shown in FIG. 5. The [M +H]$^+$ at m/z of 562.0714 is consistent with the formula for Compound I (the free base). The fragmentation behavior of M+H was studied by collisional-induced dissociation (CID). Nitrogen was used as the collision gas. All fragments were in good correlation with the structure of Compound I.

Figure 6:
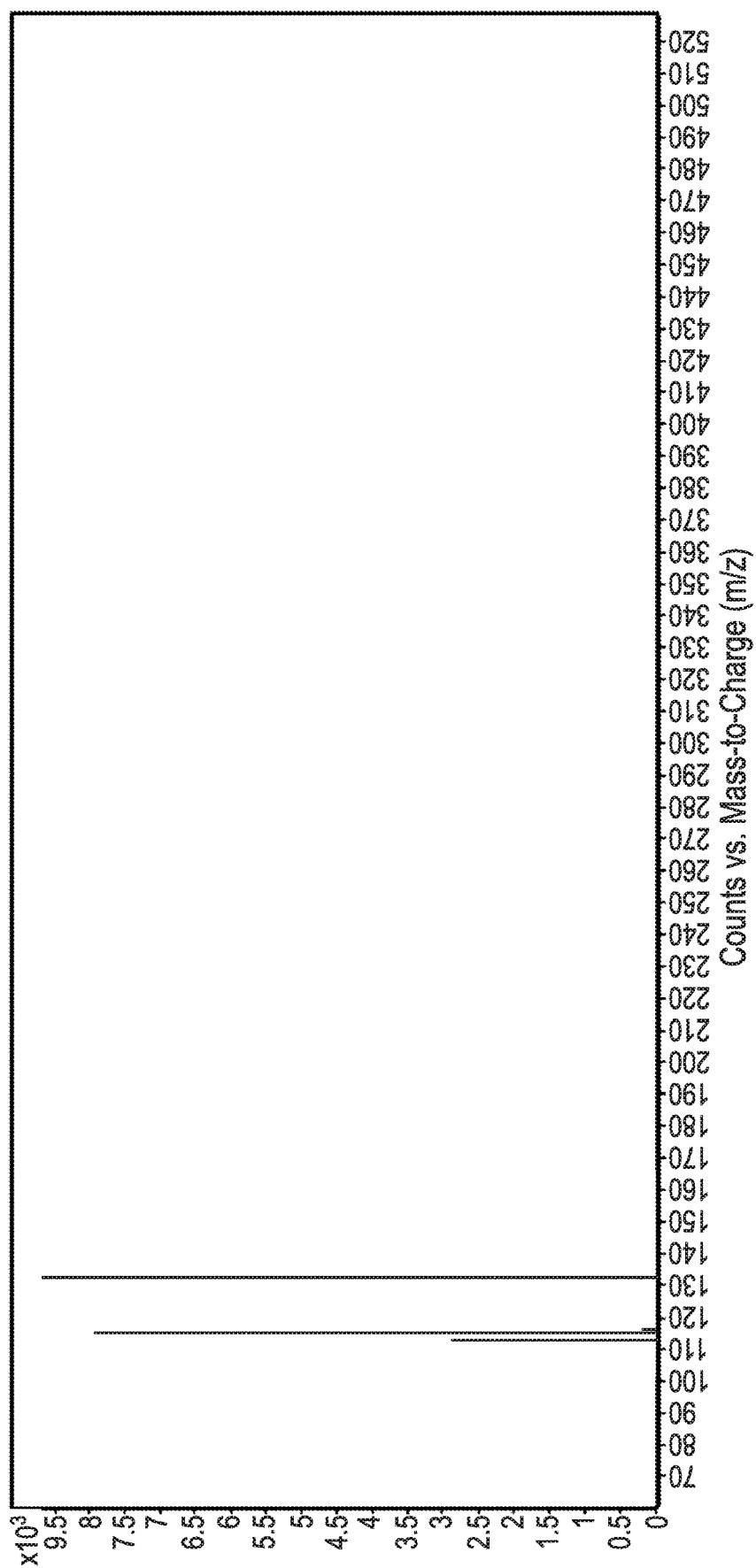
FIG. 6 shows the negative electrospray mass spectrum for the crystalline fumarate salt of Compound I, designated as Form A.

The negative electrospray mass spectrum (FIG. 6) obtained for the fumarate salt Compound I [M−H]$^+$ was found at m/z=115.0045 (calculated: m/z=115.0037; difference m/z=0.0008), indicative of the presence of fumarate counterion.

Crystal Structure Analysis of the Fumarate Salt of (S)-[3,4-difluoro-2-(2-fluoro-4-iodophenylamino) phenyl] [3-hydroxy-3-(piperidin-2-yl) azetidin-1-yl]-methanone Form A by X-Ray Diffraction Powder X-Ray Diffraction (XRPD) Studies A single crystal was mounted in a loop and measured at ambient temperature. Data were collected at the Swiss Light Source beamline X10SA equipped with a DECTRIS Pilatus 6M detector with synchrotron radiation and data processed with the program XDS. The crystal structure was solved and refined with She1XTL (Bruker AXS, Karlsruhe).

The structure of the fumarate salt of Compound I designated as Form A incorporates one chiral center with (S)-configuration according to the Cahn-Ingold-Prelog convention. To prove the structure, a single crystal determination was performed. Single crystals were crystallized from a dilute solution in acetonitrile/water 1:1 by slow evaporation of the solvent. To prove that conformation did not change through crystallization, chiral high-performance liquid chromatography (HPLC) was performed in addition. Crystal data is summarized in Table 3.

TABLE 3

| Form A Crystal Data | | |
|---|---|---|
| Form | — | A |
| Crystal System | — | Tetragonal |
| Space Group | — | P4$_3$2$_1$2 |
| Crystal Habit | — | Plates |
| Unit Cell | [Å] | a = 7.8825 |
| Dimensions | [Å] | b = 7.8825 |
| | [Å] | c = 76.846 |
| | [°] | α = 90 |
| | [°] | β = 90 |
| | [°] | γ = 90 |
| Temperature | [K] | 293 |
| Cell Volume | [Å$^3$] | 4774.7 |
| Molecules in Unit Cell | — | 8 |
| Density Calculated | (g/cm$^3$) | 1.637 |

The molecular conformation and the crystal structure parameters for Form A are given in Table 3. In the crystal structure of Form A, the piperidine nitrogen is protonated and the fumaric acid is deprotonated. The fumarate is coordinated by two piperidines and two OH-groups from different molecules of the active. The crystal packing is characterized by infinite intermolecular hydrogen bond chains. The configuration was confirmed to be (S) for the chiral carbon atom in the piperidine ring, as demonstrated by the absolute structure parameter (Flack parameter: 0.048, esd 0.013).

Figure 7:
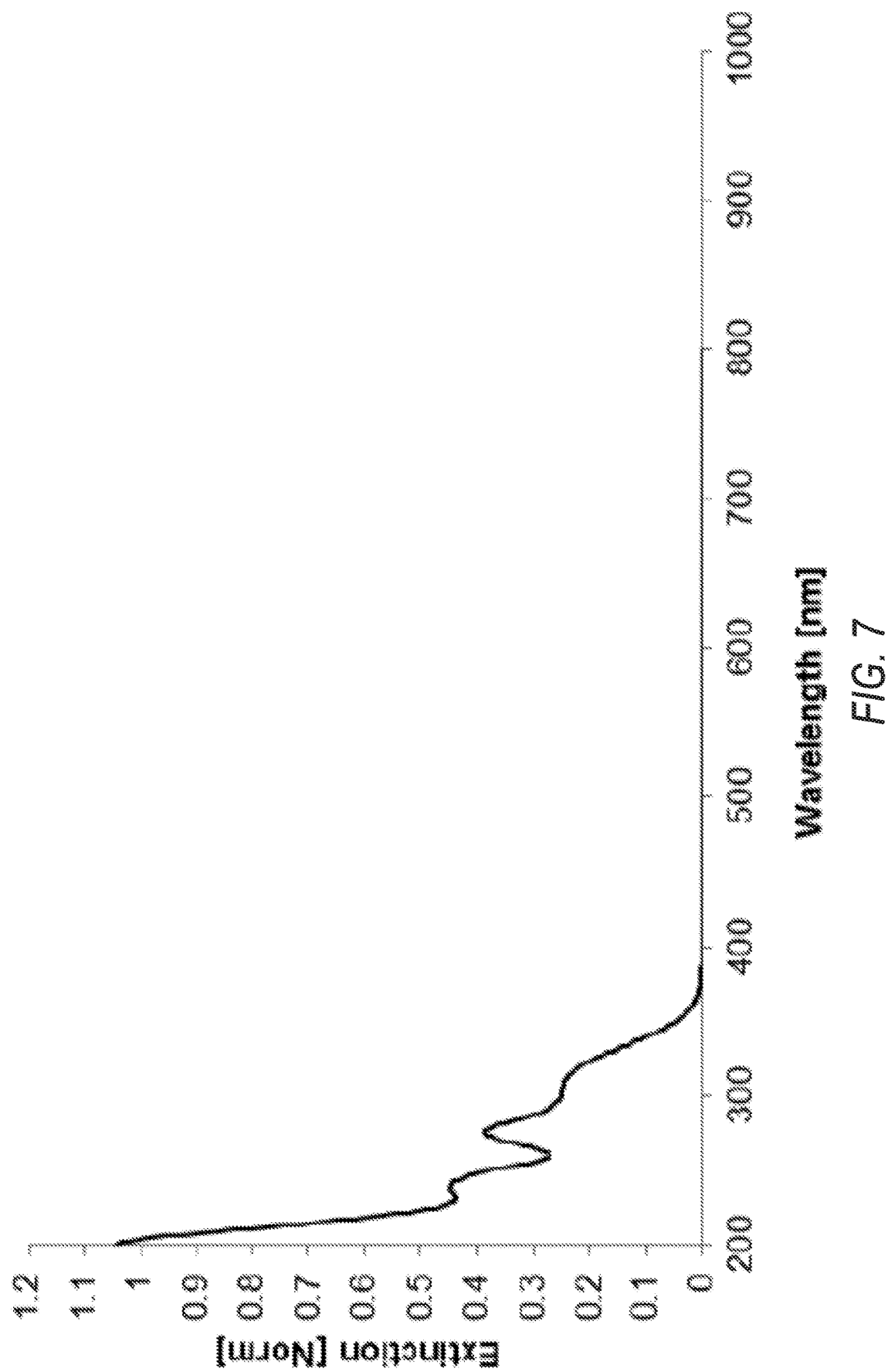
FIG. 7 shows the ultraviolet spectrum for the crystalline fumarate salt of Compound I, designated as Form A, in methanol.

Ultraviolet Spectrum for the Fumarate Salt (S)-[3, 4-difluoro-2-(2-fluoro-4-iodophenylamino)phenyl] [3-hydroxy-3-(piperidin-2-yl) azetidin-1-yl]-methanone The UV-Vis absorption maxima around 200 nm, 239 nm, 276 nm, and 310 nm are indicative of the π→π* transitions of the aromatic ring moieties and the n→π* lone pair electrons, respectively. The spectrum in FIG. 7 is consistent with the structure of the fumarate salt of Compound I and shows the characteristics expected of the chromophores present in the structure.

Structure Elucidation for the Fumarate Salt (S)-[3, 4-difluoro-2-(2-fluoro-4-iodophenylamino)phenyl] [3-hydroxy-3-(piperidin-2-yl) azetidin-1-yl]-methanone: Polymorphism More than 15 salt forms of Compound I were evaluated for their suitability for clinical development, including, for example, salts prepared from benzoic acid, malonic acid, fumaric acid, mandelic acid, acetic acid, and orotic acid. Where benzoic acid, malonic acid, mandelic acid, acetic acid, and orotic acid formed amorphous salts, crystalline salts, or mixtures of amorphous and crystalline salts depending on the solvent and conditions, the salt prepared from fumaric acid was found to be the most desirable as described below.

Comprehensive screening for crystalline solid forms of the fumarate salt of Compound I revealed one crystalline form (Form A) and one amorphous form (the amorphous form). Form A, which is solvent-free and non-hygroscopic, is the thermodynamically stable form and is the form consistently produced by the manufacturing process. The amorphous form is non-crystalline and hygroscopic. The amorphous form has been observed to convert to Form A by heating and by solvent mediated phase transition in water. In approximately 3000 crystallization experiments performed during polymorphism screenings, no additional polymorphic form was observed. Based on DSC measurements as well as temperature-controlled XRPD, no conversion of the polymorphic form is observable under heating until melting occurs. In a slurry experiment using process conditions (solvent 2-propanol/water 88:12, temperature: 20° C.), the amorphous form converted rapidly into Form A. Under heating, the amorphous form starts to convert into Form A between 90° C. and 200° C.

Form A and the amorphous from can be distinguished by differential scanning calorimetry (DSC) and X-ray powder diffraction (XRPD). Furthermore, the differences between Form A and the amorphous from have also been demonstrated using Raman spectroscopy and $^{13}C$ solid-state nuclear magnetic resonance (NMR) spectroscopy.

Differential Scanning Calorimetry (DSC)

DSC thermograms were recorded using a Mettler-Toledo instrument (DSC820/821e/1; FRS05 sensor). Approximately 2-6 mg of the sample were placed in aluminum pans and sealed with aluminum lids. Lids were automatically pierced prior to heating. Generally, samples under nitrogen were heated at a rate of 10 K/min to a maximum of 250° C.

Crystalline Form A underwent melting at 239.6° C. ($T_{onset}$). Since melting and decomposition are overlapping, the heat of fusion and $T_{extra.pol}$ were not determined (FIG. 8).

Figure 9:
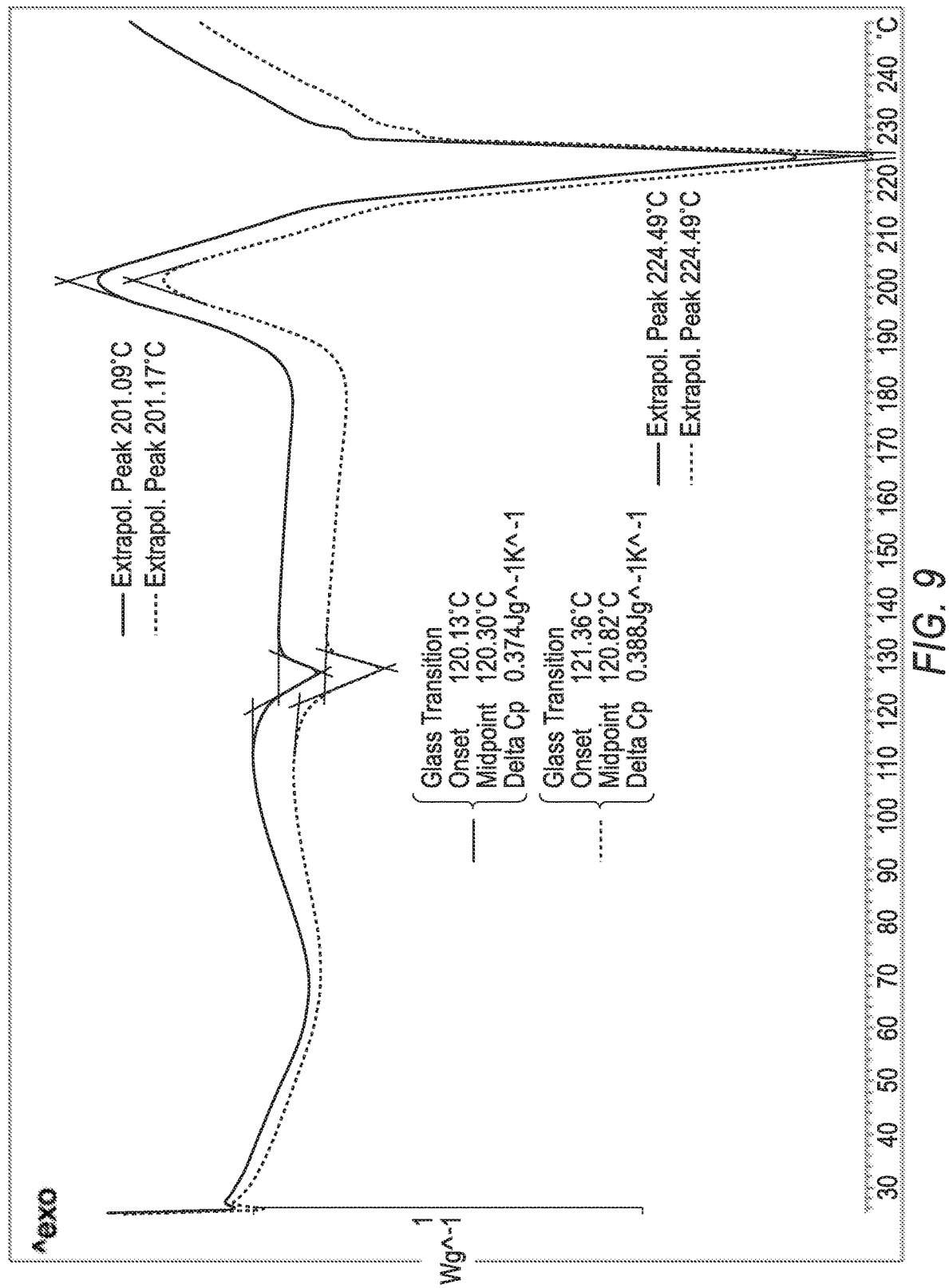
FIG. 9 shows the shows the differential scanning calorimetry trace for the fumarate salt of Compound I, designated as the amorphous form.

The Amorphous form exhibited a glass transition at 116.2° C. (from grinding) and at 120.6° C. (from freeze-drying), followed by an exothermic event due to crystallization between 150° C. and 200° C. to Form A. Above approximately 225° C., the material starts to melt (FIG. 9).

X-Ray Powder Diffraction of Form A and the Amorphous Form

X-ray diffraction patterns were recorded at ambient conditions in transmission geometry with a STOE STADI P diffractometer (Cu K α radiation [1.54 Å], primary monochromator, silicon strip detector, angular range 3° to 42° 2-θ, approximately 30 minutes total measurement time). The samples were prepared and analyzed without further processing (e.g., grinding or sieving) of the substance.

Figure 11:
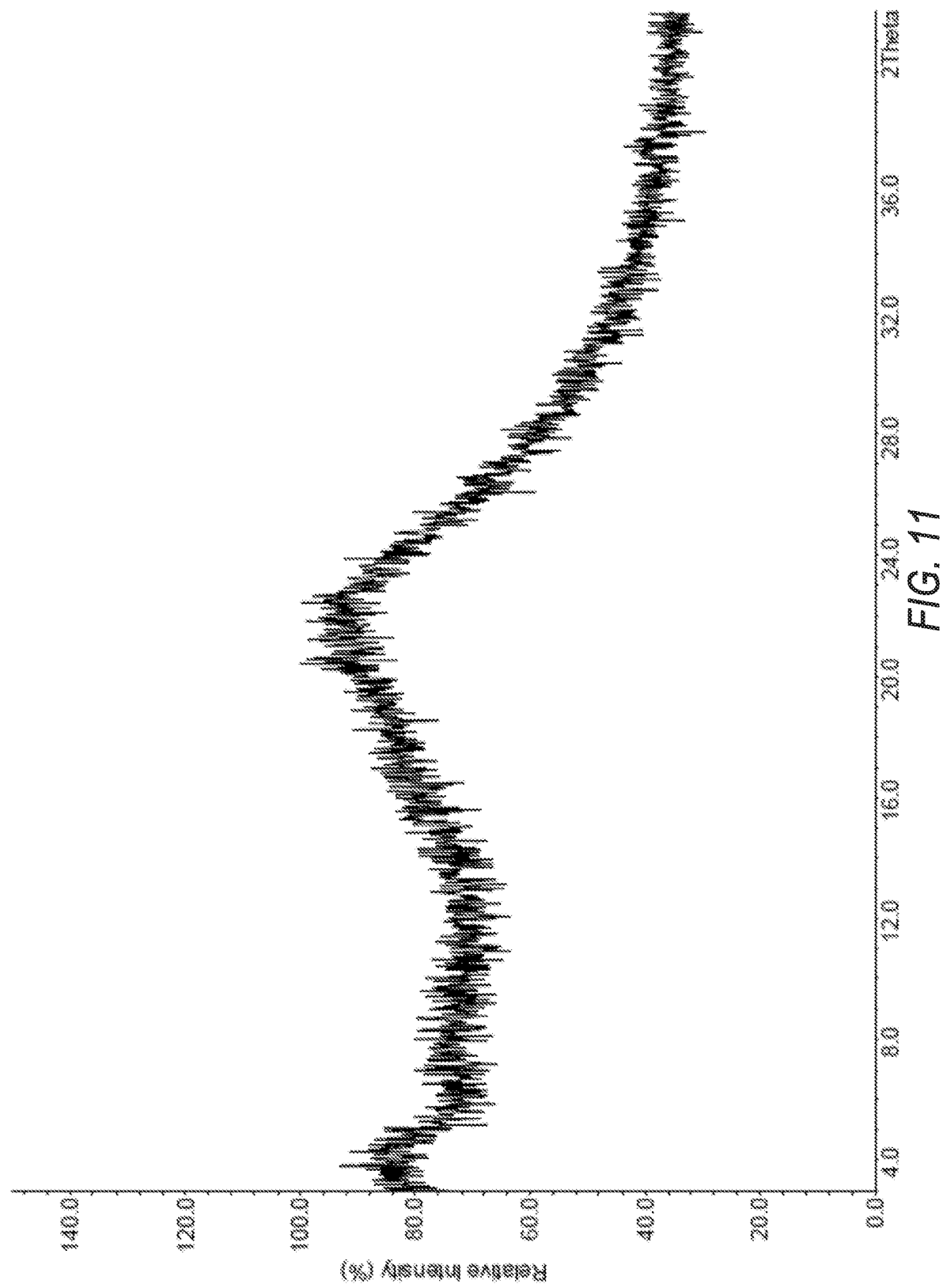
FIG. 11 shows the XRPD diffactogram for the fumarate salt of Compound I, designated as the amorphous form.

As shown in Table 4, crystalline Form A is selectively identified by a set of characteristic diffraction peak positions expressed in 2-θ value. XRPD diffractograms characteristic for the individual forms are shown in FIG. 10 and FIG. 11.

TABLE 4

| 2-θ Values for Form A (+/−0.2θ) |
| --- |
| 4.6 |
| 12.1 |
| 13.2 |
| 13.8 |
| 14.5 |
| 16.3 |
| 16.6 |
| 17.8 |
| 18.5 |
| 19.7 |
| 21.1 |

TABLE 4-continued

| 2-θ Values for Form A (+/−0.2θ) |
| --- |
| 22.6 |
| 23.0 |
| 23.3 |
| 24.5 |

Intrinsic Dissolution Rate of Crystalline Form A and the Amorphous Form

For each intrinsic dissolution measurement, a pellet was produced from the crystalline Form A or the amorphous form sample using an applied load of approximately 15 kN into a flat disk (surface area=0.5 cm$^2$). After compaction, each pellet was checked by XRPD to confirm that no polymorphic transformation had occurred during the pelleting process. The experimental conditions that were employed are summarized in Table 5.

TABLE 5

| Test Method | According to USP <1088> |
| --- | --- |
| Test Volume | 0.05M Acetate Buffer, pH = 4.5 |
| Sample (pellet) | 500 mL |
| RPM | 100 |
| Temperature | 37 C. |
| Analytical Method | Online UV spectroscopy (at 278 nm) |

Batches of Form A and the amorphous form (from freeze-drying) were used to determine the intrinsic dissolution rate of both solid forms. Intrinsic dissolution allows the characterization of different crystal forms by exposing a constant surface area to the dissolution medium. The results are summarized in Table 6.

TABLE 6

| Form | Intrinsic Dissolution Rate (mg*cm−2*min−1) |
| --- | --- |
| Form A | 0.0756 |
| the amorphous form | 2.6996 |

The intrinsic dissolution rate of both forms is very different. Based on the data, the amorphous form possesses an approximately 35 times faster intrinsic dissolution rate than crystalline Form A.

Hygroscopicity of Crystalline Form A and the Amorphous Form

Moisture sorption/desorption data were collected on a DVS-1/DVS-HT/DVS-intrinsic (SMS Surface Measurements Systems) moisture balance system. The sorption/desorption isotherms were measured stepwise in a range of 0% RH (relative humidity) to 90% RH at 25° C. A weight change of <0.002 mg/min was chosen as a criterion to switch to the next level of RH (with a maximum equilibration time of 24 hours, if the weight criterion was not met). The data were corrected for the initial moisture content of the samples; that is, the weight after drying the sample at 0% RH was taken as the zero point. The hygroscopicity of a given substance is characterized by the increase in mass when the RH was raised from 0% RH to 90% RH as given in Table 7.

TABLE 7

| Characterization of Substance | Weight Increase Δm 0% RH to 90% RH |
|---|---|
| Non-hygroscopic | Δm < 0.2% |
| Slightly hygroscopic | 0.2% ≤ Δm < 2.0% |
| Hygroscopic | Δm≤ |
| Very hygroscopic | Δm≥ |
| Deliquescent | Sufficient liquid is adsorbed to form a liquid |

Figure 12:
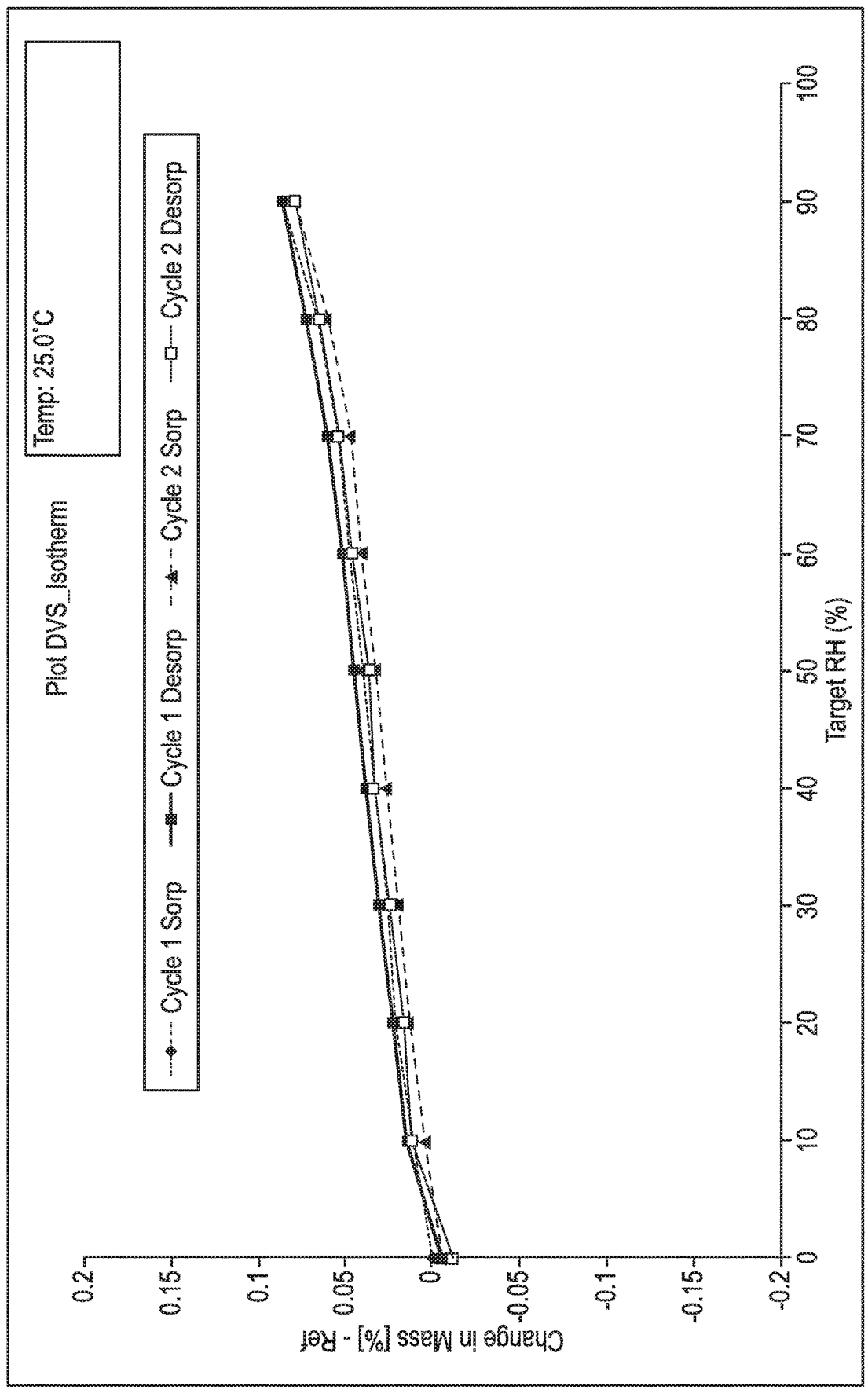
FIG. 12 depicts the dynamic moisture sorption/desorption isotherm for crystalline fumarate salt of Compound I, designated as Form A, at 25° C.

Moisture adsorption/desorption data for crystalline Form A are provided in FIG. 12. During the time scale of standard dynamic vapor sorption experiments, no conversion was observed. Between 0% RH and 90% RH, Form A exhibits a minimal and reversible weight gain or loss of ± 0.1% and is therefore classified as nonhygroscopic.

Figure 13:
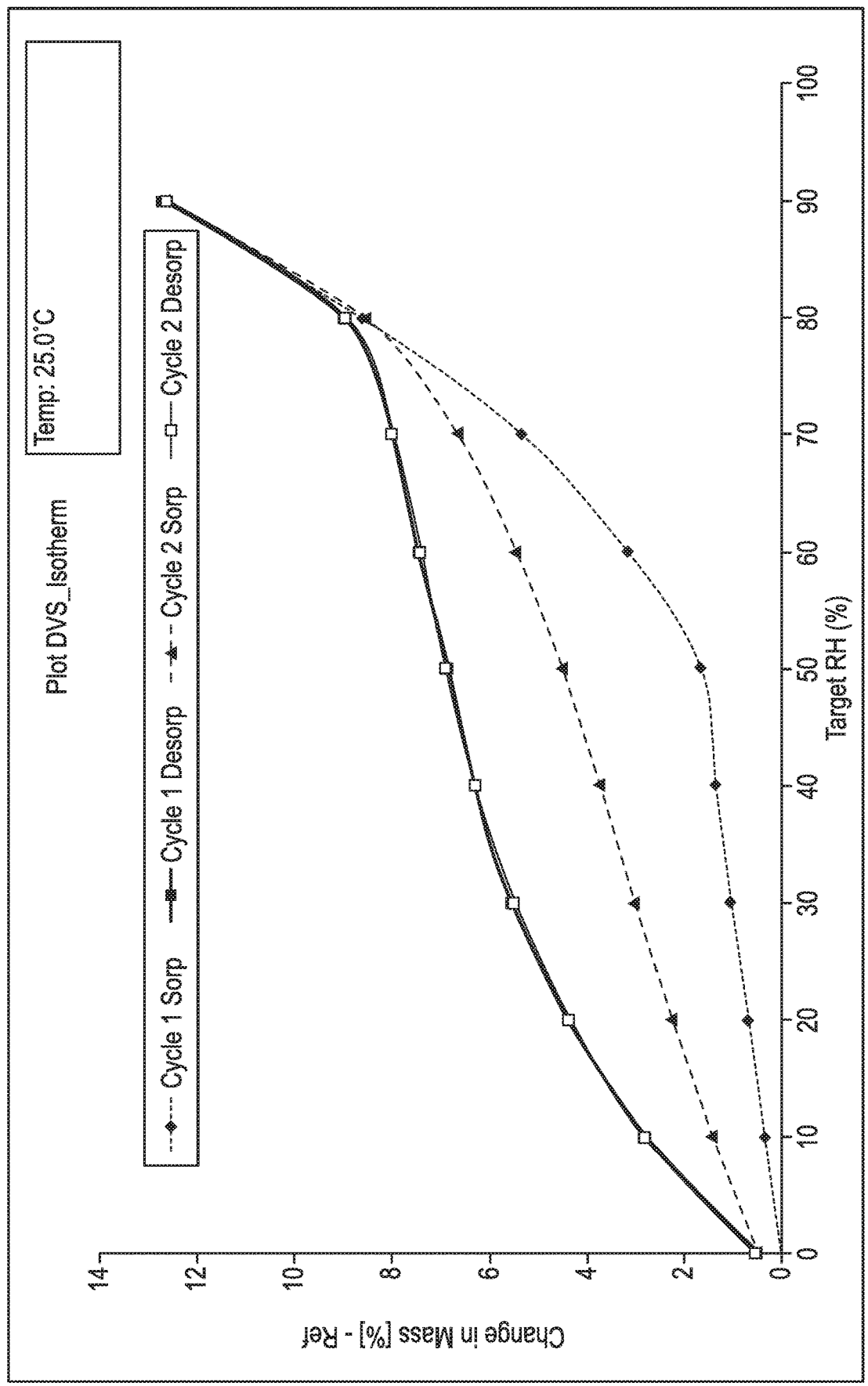
FIG. 13 depicts the dynamic moisture sorption/desorption isotherm for fumarate salt of Compound I, designated as the amorphous form, at 25° C.

Moisture sorption/desorption data of the amorphous from are provided in FIG. 13 (from freeze-drying). During the time scale of standard dynamic vapor sorption experiments, no conversion was observed. Between 0% RH and 90% RH, the amorphous from exhibits a reversible weight gain or loss of ± 12.1% and is therefore classified as hygroscopic.

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A hemifumarate salt of (S)[3,4-difluoro-2-(2-fluoro-4-iodophenylamino)phenyl] [3-hydroxy-3-(piperidin-2-yl) azetidin-1-yl]-methanone having the formula:

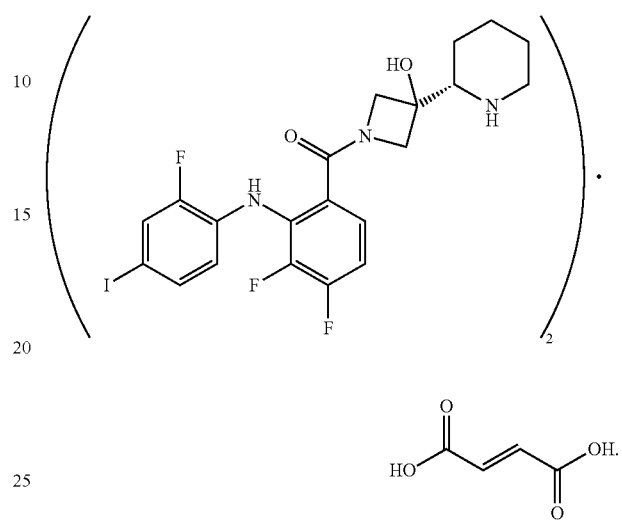

2. The hemifumarate salt of claim 1, wherein the salt is amorphous.

3. The hemifumarate salt of claim 1, wherein the salt is crystalline.

4. A pharmaceutical composition comprising a hemifumarate salt of (S)-[3,4-difluoro-2-(2-fluoro-4-iodophenylamino)phenyl] [3-hydroxy-3-(piperidin-2-yl)azetidin-1-yl]-methanone having the formula:

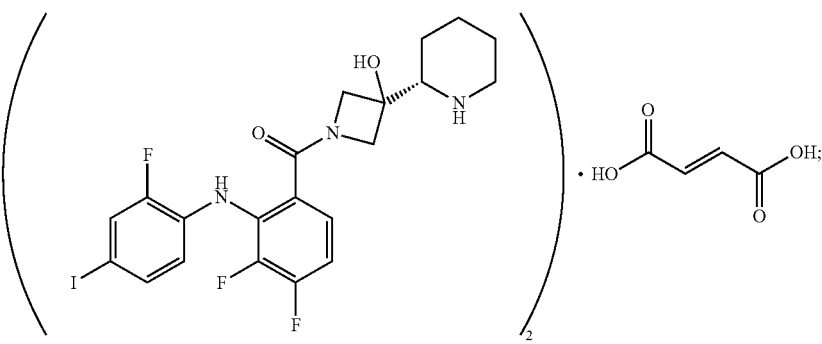

and a pharmaceutically acceptable excipient.

5. The pharmaceutical composition of claim 4, wherein the hemifumarate salt is amorphous.

6. The pharmaceutical composition of claim 4, wherein the hemifumarate salt is crystalline.

7. A method of treating cancer in a subject, the cancer chosen from melanoma, breast cancer, colorectal cancer, non-small cell lung cancer, acute myeloid leukemia, and pancreatic cancer, said method comprising administering to a subject in need of the treatment a therapeutically effective amount of a hemifumarate salt of (S)-[3,4-difluoro-2-(2-fluoro-4-iodophenylamino)phenyl] [3-hydroxy-3-(piperidin-2-yl) azetidin-1-yl]-methanone having the formula:

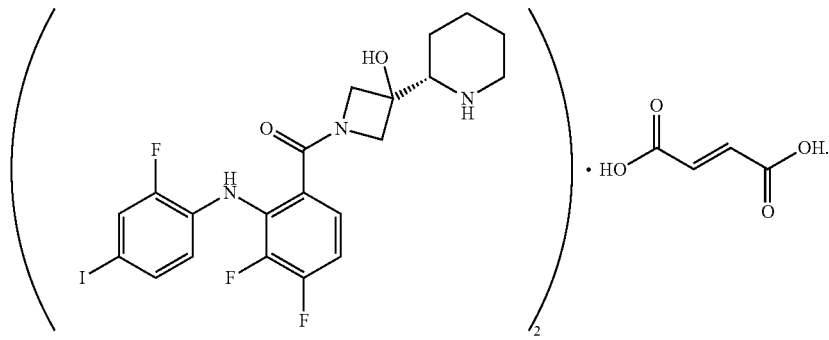

8. The method of claim 7, wherein the cancer is selected from the group consisting of BRAF V600 mutant melanoma, triple negative breast cancer, and KRAS mutant colorectal cancer.

9. The method of claim 7, wherein the cancer is BRAF V600 mutant melanoma.

10. The method of claim 7, wherein the hemifumarate salt is amorphous.

11. The method of claim 7, wherein the hemifumarate salt is crystalline.

12. A method of treating BRAF V600 mutant melanoma in a subject, the method comprising:
administering to the subject in need of the treatment a therapeutically effective amount of a hemifumarate salt of (S)- 8 3,4-difluoro-2-(2-fluoro-4-iodophenylamino) phenyl] [3-hydroxy-3-(piperidin-2-yl) azetidin-1-yl]-methanone having the formula

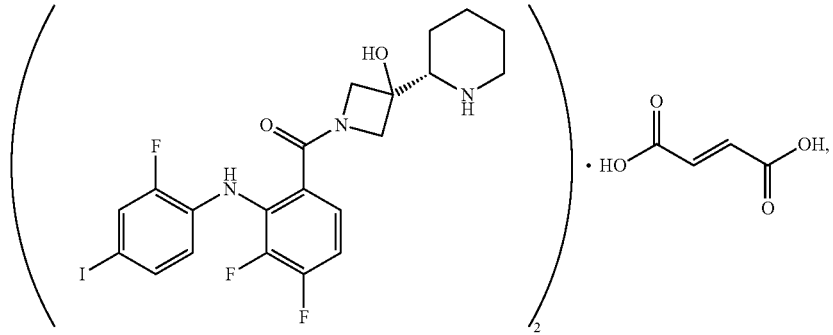

in combination with vemurafenib.

13. The method of claim 12, wherein the administering of the hemifumarate salt of (S)-[3,4-difluoro-2-(2-fluoro-4-iodophenylamino)phenyl] [3-hydroxy-3-(piperidin-2-yl) azetidin-1-yl]-methanone takes place prior or subsequent to, or concurrent with vemurafenib.

14. The method of claim 12, wherein the hemifumarate salt is amorphous.

15. The method of claim 12, wherein the hemifumarate salt is crystalline.

* * * * *